US008815770B2

(12) United States Patent
Elliott et al.

(10) Patent No.: US 8,815,770 B2
(45) Date of Patent: Aug. 26, 2014

(54) COLOR-STABLE SUPERABSORBER

(75) Inventors: Mark Elliott, Ludwigshafen (DE); Thomas Daniel, Waldsee (DE); Norbert Herfert, Altenstadt (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 13/395,051

(22) PCT Filed: Sep. 14, 2010

(86) PCT No.: PCT/EP2010/063419
§ 371 (c)(1),
(2), (4) Date: Mar. 8, 2012

(87) PCT Pub. No.: WO2011/032922
PCT Pub. Date: Mar. 24, 2011

(65) Prior Publication Data
US 2012/0178621 A1  Jul. 12, 2012

(30) Foreign Application Priority Data
Sep. 17, 2009  (EP) .................................... 09011845

(51) Int. Cl.
*B01J 20/26*  (2006.01)
*C08K 5/098*  (2006.01)
*C08K 5/00*  (2006.01)

(52) U.S. Cl.
CPC ................. *C08K 5/098* (2013.01); *C08K 5/005* (2013.01); *A61L 2400/10* (2013.01); *C08K 5/0025* (2013.01)
USPC ........................................................ 502/402

(58) Field of Classification Search
CPC ...... B01J 20/32; B01J 20/26; B01J 20/28026; B01J 20/2803; A61L 15/60
USPC ......................... 502/402; 525/329.7; 526/240
See application file for complete search history.

(56) References Cited

U.S. PATENT DOCUMENTS

| | | | |
|---|---|---|---|
| 3,992,348 A | 11/1976 | Jones et al. | |
| 7,504,551 B2 | 3/2009 | Herfert et al. | |
| 7,947,771 B2 | 5/2011 | Riegel et al. | |
| 2004/0236049 A1 | 11/2004 | Fuchs et al. | |
| 2005/0085604 A1 | 4/2005 | Handa et al. | |
| 2007/0293632 A1 | 12/2007 | Riegel et al. | |
| 2008/0114140 A1 | 5/2008 | Daniel et al. | |
| 2009/0192035 A1 | 7/2009 | Stueven et al. | |
| 2010/0041550 A1 | 2/2010 | Riegel et al. | |
| 2010/0286287 A1 | 11/2010 | Walden | |
| 2011/0015601 A1 | 1/2011 | Loeker et al. | |
| 2011/0042612 A1 | 2/2011 | Riegel et al. | |
| 2011/0118114 A1 | 5/2011 | Riegel et al. | |

FOREIGN PATENT DOCUMENTS

| | | |
|---|---|---|
| EP | 386 897 A2 | 9/1990 |
| EP | 441 975 A1 | 8/1991 |
| EP | 0 505 163 A1 | 9/1992 |
| EP | 605 215 A1 | 7/1994 |
| EP | 668 080 A2 | 8/1995 |
| EP | 1 570 869 A1 | 9/2005 |
| EP | 1 577 349 A1 | 9/2005 |
| EP | 1 645 596 A1 | 4/2006 |
| JP | 05 086251 A | 4/1993 |
| JP | 2000327926 A | 11/2000 |
| JP | 2006521431 A | 9/2006 |
| JP | 2008521952 A | 6/2008 |
| WO | WO-00/55245 A1 | 9/2000 |
| WO | WO-03/014172 A2 | 2/2003 |
| WO | WO-03/059962 A1 | 7/2003 |
| WO | WO-2005/011860 A2 | 2/2005 |
| WO | WO-2005/054356 A1 | 6/2005 |
| WO | WO-2005/073260 A1 | 8/2005 |
| WO | WO-2006/058682 A1 | 6/2006 |
| WO | WO-2008/009612 A1 | 1/2008 |
| WO | WO-2008/055856 A1 | 5/2008 |
| WO | WO-2008/092842 A1 | 8/2008 |
| WO | WO-2008/092843 A1 | 8/2008 |
| WO | WO-2009/060062 A1 | 5/2009 |
| WO | WO-2010/012762 A2 | 2/2010 |

OTHER PUBLICATIONS

Buchholz, Fredric L., et al. *Modern Superabsorbent Polymer Technology*, "Solution Polymerization: Unit Operations and Their Effect on Product Quality." New York: John Wiley & Sons, Inc., 1998, pp. 71-103.
International Search Report in International Application No. PCT/EP2010/063419, dated Dec. 6, 2010 (English translation).

*Primary Examiner* — Colleen Dunn
*Assistant Examiner* — Haytham Soliman
(74) *Attorney, Agent, or Firm* — Marshall Gerstein & Borun LLP

(57) ABSTRACT

A superabsorbent produced by polymerizing a monomer mixture which comprises at least one ethylenically unsaturated monomer bearing at least one acid group, at least 0.1% by weight and at most 20% by weight, based on the total amount of ethylenically unsaturated monomers bearing at least one acid group (calculated as the free acid), of at least one alkaline earth metal salt (calculated without water of crystallization) selected from the salts of calcium, strontium or barium having been added before or during the polymerization and/or, if the polymerization is followed by a separate drying step, to the polymer before the drying, exhibits improved stability to discoloration in the course of storage under elevated temperatures and/or elevated air humidity.

19 Claims, No Drawings

COLOR-STABLE SUPERABSORBER

CROSS-REFERENCE TO RELATED APPLICATIONS

This is the U.S. national phase of International Application No. PCT/EP2010/063419, filed Sep. 14, 2010, which claims the benefit of European Patent Application No. 09011845.6, filed Sep. 17, 2009.

The present invention relates to a color-stable superabsorbent, to a process for producing it and to the use thereof and to hygiene articles comprising it. A color-stable superabsorbent is understood to mean a superabsorbent which is discolored only to a minor degree, if at all, in the course of storage under elevated temperature and air humidity.

Superabsorbents are known. For such materials, names such as "high-swellability polymer", "hydrogel" (often also used for the dry form), "hydrogel forming polymer", "water-absorbing polymer", "absorbent gel-forming material", "swellable resin", "water-absorbing resin" or the like are also in common use. The substances in question are crosslinked hydrophilic polymers, especially polymers of (co)polymerized hydrophilic monomers, graft (co)polymers of one or more hydrophilic monomers on a suitable graft base, crosslinked cellulose ethers or starch ethers, crosslinked carboxymethylcellulose, partly crosslinked polyalkylene oxide or natural products which are swellable in aqueous liquids, for example guar derivatives, of which water-absorbing polymers based on partly neutralized acrylic acid are the most widespread. The essential properties of superabsorbents are their abilities to absorb several times their own weight of aqueous liquids and not to release the liquid again even under a certain pressure. The superabsorbent, which is used in the form of a dry powder, is converted to a gel when it absorbs liquid, and correspondingly to a hydrogel when it absorbs water as usual. Crosslinking is essential for synthetic superabsorbents and is an important difference from customary pure thickeners, since it leads to the insolubility of the polymers in water. Soluble substances would not be usable as superabsorbents. By far the most important field of use of superabsorbents is the absorption of body fluids. Superabsorbents are used, for example, in diapers for infants, incontinence products for adults or feminine hygiene products. Other fields of use are, for example, as water-retaining agents in market gardening, as water stores for protection from fire, for liquid absorption in food packaging, or quite generally for absorbing moisture.

Superabsorbents can absorb several times their own weight of water and retain it under a certain pressure. In general, such a superabsorbent has a CRC ("centrifuge retention capacity", see below for test method) of at least 5 g/g, preferably at least 10 g/g and more preferably at least 15 g/g. A "superabsorbent" may also be a mixture of different individual superabsorbent substances or a mixture of components which exhibit superabsorbent properties only when they interact; it is not so much the substance composition as the superabsorbent properties that are important here.

What is important for a superabsorbent is not just its absorption capacity but also the ability to retain liquid under pressure (retention, usually expressed as "absorption under load" (AUL) or "absorption against pressure" (AAP), see below for test method) and liquid transport in the swollen state (usually expressed as "saline flow conductivity" (SFC), see below for test method). Swollen gel can hinder or prevent liquid transport to as yet unswollen superabsorbent ("gel blocking"). Good transport properties for liquids are possessed, for example, by hydrogels which have a high gel strength in the swollen state. Gels with only a low gel strength are deformable under an applied pressure (body pressure), block pores in the superabsorbent/cellulose fiber suction body and thus prevent further absorption of liquid. An increased gel strength is generally achieved through a higher degree of crosslinking, which, however, reduces the absorption capacity of the product. An elegant method of increasing the gel strength is that of increasing the degree of crosslinking at the surface of the superabsorbent particles compared to the interior of the particles. To this end, superabsorbent particulars which have usually been dried in a surface postcrosslinking step and have an average crosslinking density are subjected to additional crosslinking in a thin surface layer of the particles thereof. The surface postcrosslinking increases the crosslinking density in the shell of the superabsorbent particles, which raises the absorption under compressive stress to a higher level. While the absorption capacity in the surface layer of the superabsorbent particles falls, their core, as a result of the presence of mobile polymer chains, has an improved absorption capacity compared to the shell, such that the shell structure ensures improved liquid conduction, without occurrence of gel blocking. It is likewise known that superabsorbents which are relatively highly crosslinked overall can be obtained and the degree of crosslinking in the interior of the particles can subsequently be reduced compared to an outer shell of the particles.

Processes for producing superabsorbents are also known. Superabsorbents based on acrylic acid, which are the most common on the market, are produced by free-radical polymerization of acrylic acid in the presence of a crosslinker (the "internal crosslinker"), the acrylic acid being neutralized to a certain degree before, after or partly before and partly after the polymerization, typically by adding alkali, usually an aqueous sodium hydroxide solution. The polymer gel thus obtained is comminuted (according to the polymerization reactor used, this can be done simultaneously with the polymerization) and dried. The dry powder thus obtained (the "base polymer") is typically postcrosslinked on the surface of the particles, by reacting it with further crosslinkers, for instance organic crosslinkers or polyvalent cations, for example aluminum (usually used in the form of aluminum sulfate) or both, in order to obtain a more highly crosslinked surface layer compared to the particle interior.

A problem which often occurs in the case of superabsorbents is discoloration, which occurs in the course of storage under elevated temperature or elevated air humidity. Such conditions often occur in the case of storage of superabsorbents in tropical or subtropical countries. Superabsorbents tend to yellow under such conditions; they may even assume a brown or even almost black color. This discoloration of the actually colorless superabsorbent powder is unsightly and undesired, since it is visible especially in the desired thin hygiene products, and consumers reject unsightly hygiene products. The cause of the discoloration has not been entirely clarified, but reactive compounds such as residual monomers from the polymerization, the use of some initiators, impurities in the monomer or the neutralizing agent, surface postcrosslinkers or stabilizers in the monomers used appear to play a role.

Fredric L. Buchholz and Andrew T. Graham (eds.) give, in: "Modern Superabsorbent Polymer Technology", J. Wiley & Sons, New York, U.S.A./Wiley-VCH, Weinheim, Germany, 1997, ISBN 0-471-19411-5, a comprehensive overview of superabsorbents, properties thereof and processes for producing superabsorbents. It is also mentioned there, in section 2.7.2, that calcium ions are known as ionic crosslinkers of superabsorbents, but only trivalent ions such as aluminum are usable crosslinkers.

WO 2005/073 260 A1 discloses that, in the case of production of superabsorbents by polymerization of oversaturated solutions, sodium acrylate monomer may be replaced completely or partially by salts such as magnesium acrylate, calcium acrylate, strontium acrylate or barium acrylate. WO 2005/011860 divides the known internal crosslinkers for superabsorbents into different crosslinker classes, one of which encompasses polyvalent metal cations. This includes, as divalent cations, magnesium, calcium and strontium, but preference is given overall to the trivalent aluminum.

WO 2008/055856 A1 teaches the prevention of discoloration of a superabsorbent which is caused by an excessively high iron content of sodium hydroxide solution which is used for partial neutralization of the acrylic acid in the course of preparation of the superabsorbent, by adding phosphoric acid or phosphate salts. JP 05/086 251 A teaches the use of phosphoric acid derivatives or salts thereof, especially 1-hydroxyethylidene-1,1-diphosphonic acid, ethylenediaminetetra(methylenephosphonic acid), diethylenetriaminepenta(methylenephosphonic acid) or the alkali metal or ammonium salts thereof as stabilizers of superabsorbents against discoloration. WO 03/059 962 A1 or the equivalent patent application US 2005/0085604 A1 discloses the use of metal chelating agents in any step of superabsorbent production, and the addition of a reducing or oxidizing agent before drying of the water-containing polymer as measures against discoloration. WO 03/014 172 A2 relates to the use of superabsorbents formed from high-purity acrylic acid, which have been freed especially of aldehydes to prevent discoloration of the superabsorbents. WO 00/55245 A1 teaches the stabilization of superabsorbents against discoloration by treatment with an inorganic reducing agent and optionally a metal salt, for instance an alkaline earth metal salt, which is added after the polymerization. The inorganic reducing agent is typically a hypophosphite, phosphite, bisulfite or sulfite. The metal salt is typically a colorless (the property of "colorless" is often also simply referred to as "white") phosphate, acetate or lactate, but not a halide. According to the teaching of WO 2006/058 682, discoloration of superabsorbents is avoided when the drying and the postcrosslinking reaction are carried out in an atmosphere which is essentially free of oxidizing gases.

EP 505 163 A1 discloses the use of a combination of surface-active substance and a compound which adds onto double bonds, for example unsubstituted or substituted alkyl- or arylsulfinic acids or salts thereof to reduce the level of residual monomers in superabsorbents. EP 668 080 A2 and the partial application EP 1570 869 A1 relate to the use of organic acids, including sulfinic acids, but exclusively of salts of organic acids or sulfinic acids, or of polyamino acids or salts thereof, for reducing the level of residual surface postcrosslinker, especially of epoxy compounds used as surface postcrosslinkers, after the surface postcrosslinking. EP 386 897 A2, EP 441 975 A1 and EP 605 215 A1 teach the use of sulfites, hydrogensulfites or thiosulfates to reduce the level of residual monomers from the polymerization. EP 1 645 596 A1 teaches the stabilization of superabsorbents against discoloration by addition of an inorganic salt, of an aminocarboxy acid chelating agent and of an organic antioxidant. The inorganic salts used are sulfites, bisulfites, pyrosulfites, dithionites, trithionates, tetrathionates, thiosulfates or nitrites. EP 1 577 349 A1 teaches the use of these salts for the same purpose, although the iron content of the superabsorbents treated therewith is kept below 1 ppm by weight.

WO 2009/060062 or the prior international patent application PCT/EP2009/059793 teach the addition of sulfinic acid derivatives to superabsorbents in order to stabilize them against discoloration. WO 2008/092 842 A1 teaches the addition of a basic salt of a divalent metal cation to superabsorbents, in order to increase the stability to discoloration among other reasons. WO 2008/092 843 A1 discloses the use of carboxylic salts and/or basic salts of trivalent metal cations for the same purpose. WO 2005/054 356 A1 teaches the use of sterically hindered phenols instead of the industrially customary para-methoxyphenol ("methylhydroquinone", "MEHQ") as stabilizers for acrylic acid against polymerization, which have the advantage of lower discoloration of the polymer.

It is an object of the present invention to find other superabsorbents or superabsorbents which are stabilized even better to discoloration, especially to yellowing or browning in the course of storage under elevated temperature and/or elevated air humidity. If at all, this should only insignificantly impair the use properties of the superabsorbent, especially its absorption capacity for fluid, including under pressure, and its ability to conduct fluid. Equally, further properties should not be impaired, for instance odor, which may be a problem in the case of sulfur-containing reducing agents in the presence of moisture, or the free flow thereof, which may be a problem in the case of sodium hypophosphite addition, or dust formation, which may be a problem in the case of addition of insoluble calcium salts. Further objects of the invention are the finding of a process for producing such a superabsorbent, and uses of this superabsorbent.

This object is achieved by a superabsorbent produced by polymerizing a monomer mixture which comprises at least one ethylenically unsaturated monomer bearing at least one acid group, at least 0.1% by weight and at most 20% by weight, based on the total amount of ethylenically unsaturated monomers bearing at least one acid group (calculated as the free acid), of at least one alkaline earth metal salt (calculated without water of crystallization) selected from the salts of calcium, strontium or barium having been added before or during the polymerization and/or, if the polymerization is followed by a separate drying step, to the polymer before the drying. Additionally found have been a process for producing this superabsorbent, uses of this superabsorbent and hygiene articles which comprise this superabsorbent and processes for production thereof.

The inventive superabsorbents exhibit surprisingly good stability to discoloration, without their use properties, such as CRC, AUL or SFC, being significantly impaired.

At least one water-soluble alkaline earth metal salt selected from the salts of calcium, strontium or barium is added to the inventive superabsorbent. It is possible to use mixtures of salts of all possible two-substance combinations of these elements, or all three of these elements. In terms of technical effect, there is no significant difference between the salts of calcium, strontium and barium, but calcium salts are most preferred for economic reasons.

The anions of the alkaline earth metal salts can in principle be selected freely, with the restriction that they must not lead to adverse effects in the superabsorbent and/or in the use thereof. Examples of suitable anions of the alkaline earth metal salts are halides, especially chloride, hydroxide, carbonate, carboxylates such as formate, acetate, propionate or lactate, nitrate or sulfate. It is also possible to use mixtures.

Preference is given to using water-soluble salts or those which, even though they are relatively sparingly soluble in water, react rapidly with the acid groups of the superabsorbent or of the monomers. Such salts have the advantage, especially in the customary preparation of the superabsorbent from water-comprising monomer mixtures, that an equivalent amount of the neutralizing agent otherwise used can be saved. The anions of the alkaline earth metal salt are selected correspondingly for that purpose, preference being given to hydroxide, carbonate or lactate.

Especially preferred alkaline earth metal salts are calcium hydroxide, strontium hydroxide, barium hydroxide, calcium carbonate, strontium carbonate, barium carbonate, calcium lactate, strontium lactate, barium lactate, calcium sulfate, strontium sulfate, barium sulfate or mixtures thereof. Particular preference is given to calcium hydroxide, calcium carbonate, calcium lactate and calcium sulfate.

The alkaline earth metal salt is generally added in an amount of at least 0.1% by weight, preferably at least 0.5% by weight and more preferably at least 1% by weight, and generally of at most 20% by weight, preferably at most 10% by weight and more preferably of at most 5% by weight, based in each case on the total amount of ethylenically unsaturated monomers bearing at least one acid group. These monomers are calculated as the free acid; any complete or partial neutralization of the acid groups is not taken into account in the calculation. Some alkaline earth metal salts may comprise water of crystallization. This is likewise not taken into account in the calculation.

The inventive superabsorbent is prepared by polymerizing a monomer mixture which comprises at least one ethylenically unsaturated monomer bearing at least one acid group. Processes for preparing superabsorbents by polymerizing a monomer mixture which comprises at least one ethylenically unsaturated monomer bearing at least one acid group are known. An inventive superabsorbent is, for example, prepared by aqueous solution polymerization of a monomer mixture comprising:

a) at least one ethylenically unsaturated monomer which bears at least one acid group and is optionally present at least partly in salt form,
b) at least one crosslinker,
c) at least one initiator,
d) optionally one or more ethylenically unsaturated monomers copolymerizable with the monomers specified under a), and
e) optionally one or more water-soluble polymers.

The monomers a) are preferably water-soluble, i.e. the solubility in water at 23° C. is typically at least 1 g/100 g of water, preferably at least 5 g/100 g of water, more preferably at least 25 g/100 g of water, most preferably at least 35 g/100 g of water.

Suitable monomers a) are, for example, ethylenically unsaturated carboxylic acids or salts thereof, such as acrylic acid, methacrylic acid, maleic acid or salts thereof, maleic anhydride and itaconic acid or salts thereof. Particularly preferred monomers are acrylic acid and methacrylic acid. Very particular preference is given to acrylic acid.

Further suitable monomers a) are, for example, ethylenically unsaturated sulfonic acids, such as styrenesulfonic acid and 2-acrylamido-2-methylpropanesulfonic acid (AMPS).

Impurities can have a considerable influence on the polymerization. The raw materials used should therefore have a maximum purity. It is therefore often advantageous to specially purify the monomers a). Suitable purification processes are described, for example, in WO 2002/055469 A1, WO 2003/078378 A1 and WO 2004/035514 A1. A suitable monomer a) is, for example, acrylic acid purified according to WO 2004/035514 A1 comprising 99.8460% by weight of acrylic acid, 0.0950% by weight of acetic acid, 0.0332% by weight of water, 0.0203% by weight of propionic acid, 0.0001% by weight of furfurals, 0.0001% by weight of maleic anhydride, 0.0003% by weight of diacrylic acid and 0.0050% by weight of hydroquinone monomethyl ether.

The proportion of acrylic acid and/or salts thereof in the total amount of monomers a) is preferably at least 50 mol %, more preferably at least 90 mol %, most preferably at least 95 mol %.

The monomer solution comprises preferably at most 250 ppm by weight, preferably at most 130 ppm by weight, more preferably at most 70 ppm by weight and preferably at least 10 ppm by weight, more preferably at least 30 ppm by weight, especially around 50 ppm by weight, of hydroquinone monoether, based in each case on the unneutralized monomer a); neutralized monomer a), i.e. a salt of the monomer a), is considered for arithmetic purposes as unneutralized monomer. For example, the monomer solution can be prepared by using an ethylenically unsaturated monomer bearing acid groups with an appropriate content of hydroquinone monoether.

Preferred hydroquinone monoethers are hydroquinone monomethyl ether (MEHQ) and/or alpha-tocopherol (vitamin E).

Suitable crosslinkers b) are compounds having at least two groups suitable for crosslinking. Such groups are, for example, ethylenically unsaturated groups which can be polymerized free-radically into the polymer chain, and functional groups which can form covalent bonds with the acid groups of the monomer a). In addition, polyvalent metal salts which can form coordinate bonds with at least two acid groups of the monomer a) are also suitable as crosslinkers b).

Crosslinkers b) are preferably compounds having at least two polymerizable groups which can be polymerized free-radically into the polymer network. Suitable crosslinkers b) are, for example, ethylene glycol dimethacrylate, diethylene glycol diacrylate, polyethylene glycol diacrylate, allyl methacrylate, trimethylolpropane triacrylate, triallylamine, tetraallylammonium chloride, tetraallyloxyethane, as described in EP 530 438 A1, di- and triacrylates, as described in EP 547 847 A1, EP 559 476 A1, EP 632 068 A1, WO 93/21237 A1, WO 2003/104299 A1, WO 2003/104300 A1, WO 2003/104301 A1 and DE 103 31 450 A1, mixed acrylates which, as well as acrylate groups, comprise further ethylenically unsaturated groups, as described in DE 103 31 456 A1 and DE 103 55 401 A1, or crosslinker mixtures, as described, for example, in DE 195 43 368 A1, DE 196 46 484 A1, WO 90/15830 A1 and WO 2002/32962 A2.

Preferred crosslinkers b) are pentaerythrityl Manyl ether, tetraallyloxyethane, methylenebismethacrylamide, 15- to 20-tuply ethoxylated trimethylolpropane triacrylate, 15- to 20-tuply ethoxylated glyceryl triacrylate, polyethylene glycol diacrylate with between 4 and 45 —CH$_2$CH$_2$O— units in the molecule chain, trimethylolpropane triacrylate and triallylamine.

Very particularly preferred crosslinkers b) are the polyethoxylated and/or -propoxylated glycerols which have been esterified with acrylic acid or methacrylic acid to give di- or triacrylates, as described, for example, in WO 2003/104301 A1. Di- and/or triacrylates of 3- to 10-tuply ethoxylated glycerol are particularly advantageous. Very particular preference is given to di- or triacrylates of 1- to 5-tuply ethoxylated and/or propoxylated glycerol. Most preferred are the triacrylates of 3- to 5-tuply ethoxylated and/or propoxylated glycerol, especially the triacrylate of 3-tuply ethoxylated glycerol.

The amount of crosslinker b) is preferably from 0.05 to 1.5% by weight, more preferably from 0.1 to 1% by weight, most preferably from 0.3 to 0.6% by weight, based in each case on monomer a). With rising crosslinker content, the centrifuge retention capacity (CRC) falls and the absorption under a pressure of 0.3 psi (AUL0.3 psi) rises.

The initiators c) may be all compounds which generate free radicals under the polymerization conditions, for example thermal initiators, redox initiators, photoinitiators. Suitable redox initiators are sodium peroxodisulfate/ascorbic acid, hydrogen peroxide/ascorbic acid, sodium peroxodisulfate/sodium bisulfite and hydrogen peroxide/sodium bisulfite. Preference is given to using mixtures of thermal initiators and redox initiators, such as sodium peroxodisulfate/hydrogen peroxide/ascorbic acid. The reducing component used is, however, preferably the mixture described in detail below of the sodium salt of 2-hydroxy-2-sulfinatoacetic acid, the disodium salt of 2-hydroxy-2-sulfonatoacetic acid and sodium bisulfite (Brüggolit® FF6M or Brüggolit® FF7).

Ethylenically unsaturated monomers d) copolymerizable with the ethylenically unsaturated monomers a) bearing acid groups are, for example, acrylamide, methacrylamide, hydroxyethyl acrylate, hydroxyethyl methacrylate, dimethylaminoethyl methacrylate, dimethylaminoethyl acrylate, dimethylaminopropyl acrylate, diethylaminopropyl acrylate, dimethylaminoethyl methacrylate, diethylaminoethyl methacrylate, maleic acid or salts thereof, and maleic anhydride.

The water-soluble polymers e) used may be polyvinyl alcohol, polyvinylpyrrolidone, starch, starch derivatives, modified cellulose, such as methylcellulose or hydroxyethyl-cellulose, gelatin, polyglycols or polyacrylic acids, preferably starch, starch derivatives and modified cellulose.

Typically, an aqueous monomer solution is used. The water content of the monomer solution is preferably from 40 to 75% by weight, more preferably from 45 to 70% by weight, most preferably from 50 to 65% by weight. It is also possible to use monomer suspensions, i.e. oversaturated monomer solutions. With rising water content, the energy requirement in the subsequent drying rises, and, with falling water content, the heat of polymerization can only be removed inadequately.

The alkaline earth metal salt (or mixture of alkaline earth metal salts) is added to the monomer mixture before or during the polymerization or, if the polymerization is followed by a separate drying step, to the polymer before the drying, or partly before or during the polymerization and partly to the polymer before the drying. What is desired is a homogeneous distribution of the alkaline earth metal salt in the superabsorbent. In principle, the alkaline earth metal salt, in terms of method and time, is mixed in as described below for the neutralizing agent. The simplest and therefore preferred method is addition to the monomer mixture before the polymerization. The alkaline earth metal salt may, however, also be introduced into the polymer gel which forms, during the polymerization or after the polymerization, but it is in any case introduced before the drying. Addition during the polymerization is possible in a simple manner in particular in the case of processes in which the material being polymerized is mixed, for example in the case of polymerization in a kneader. Addition after the polymerization and before the drying is possible in a simple manner in particular in the case of processes in which the mixture being polymerized is conducted from the polymerization into a dedicated drying step, i.e. especially in the case of all processes in which polymerization and drying are performed in separate apparatus. In this case, the alkaline earth metal salt can be mixed into the polymer gel by means of any known mixing process and apparatus.

The alkaline earth metal salt is used as a dry substance or as a solution or dispersion in a solvent. The solvent used is preferably water.

For optimal action, the preferred polymerization inhibitors require dissolved oxygen. The monomer solution can therefore be freed of dissolved oxygen before the polymerization by inertization, i.e. flowing an inert gas through, preferably nitrogen or carbon dioxide. The oxygen content of the monomer solution is preferably lowered before the polymerization to less than 1 ppm by weight, more preferably to less than 0.5 ppm by weight, most preferably to less than 0.1 ppm by weight.

The monomer mixture may comprise further components. Examples of further components used in monomer mixtures of this kind are, for instance, chelating agents, in order to keep metal ions in solution.

The acid groups of the polymer gels obtained from the polymerization have typically been partially neutralized. Neutralization is preferably carried out at the monomer stage; in other words, salts of the monomers bearing acid groups or, to be precise, a mixture of monomers bearing acid groups and salts of the monomers bearing acid groups ("partly neutralized acid") are used as component a) in the polymerization. This is typically done by mixing the neutralizing agent as an aqueous solution or preferably also as a solid into the monomer mixture intended for polymerization or preferably into the monomer bearing acid groups or a solution thereof. The degree of neutralization is preferably from 25 to 95 mol %, more preferably from 50 to 80 mol %, most preferably from 65 to 72 mol %, for which the customary neutralizing agents can be used, preferably alkali metal hydroxides, alkali metal oxides, alkali metal carbonates or alkali metal hydrogencarbonates and also mixtures thereof. Instead of alkali metal salts, it is also possible to use ammonium salts. Particularly preferred alkali metals are sodium and potassium, but very particular preference is given to sodium hydroxide, sodium carbonate or sodium hydrogencarbonate and also mixtures thereof.

However, it is also possible to carry out neutralization after the polymerization, at the stage of the polymer gel formed in the polymerization. It is also possible to neutralize up to 40 mol %, preferably from 10 to 30 mol % and more preferably from 15 to 25 mol % of the acid groups before the polymerization by adding a portion of the neutralizing agent actually to the monomer solution and setting the desired final degree of neutralization only after the polymerization, at the polymer gel stage. When the polymer gel is neutralized at least partly after the polymerization, the polymer gel is preferably comminuted mechanically, for example by means of an extruder, in which case the neutralizing agent can be sprayed, sprinkled or poured on and then carefully mixed in. To this end, the gel mass obtained can be repeatedly extruded for homogenization.

However, preference is given to performing the neutralization at the monomer stage. In other words: in a very particularly preferred embodiment, the monomer a) used is a mixture of from 25 to 95 mol %, more preferably from 50 to 80 mol %, more preferably from 65 to 72 mol %, of salt of the monomer bearing acid groups, and the remainder to 100 mol % of monomer bearing acid groups. This mixture is, for example, a mixture of sodium acrylate and acrylic acid or a mixture of potassium acrylate and acrylic acid.

In a preferred embodiment, the neutralizing agent used for the neutralization is one whose iron content is generally below 10 ppm by weight, preferably below 2 ppm by weight and more preferably below 1 ppm by weight. Likewise desired is a low content of chloride and anions of oxygen acids of chlorine. A suitable neutralizing agent is, for example, the 50% by weight sodium hydroxide solution or potassium hydroxide solution which is typically traded as "membrane grade"; even more pure and likewise suitable, but also more expensive, is the 50% by weight sodium hydroxide solution or potassium hydroxide solution typically traded as "amalgam grade" or "mercury process".

When the alkaline earth metal salt used is a water-soluble alkaline earth metal salt or one which, though of relatively sparing solubility, reacts relatively rapidly, the amount of neutralizing agent equivalent to the amount of alkaline earth metal ions added can be saved. In other words, the alkaline earth metal salt can also serve simultaneously as the neutralizing agent, in which case the divalent alkaline earth metal ion replaces two monovalent alkali metal ions. Suitable for this purpose are especially alkaline earth metal hydroxides, carbonates and lactates.

Processes for producing the superabsorbents from monomer mixtures such as those described above by way of example are also known. Suitable polymerization reactors are, for example, kneading reactors or belt reactors. In the kneader, the polymer gel which forms in the polymerization of an aqueous monomer solution or suspension is comminuted continuously by, for example, contrarotatory stirrer shafts, as described in WO 2001/38402 A1. Polymerization on the belt is described, for example, in EP 955 086 A2, DE 38 25 366 A1 and U.S. Pat. No. 6,241,928. Polymerization in a belt reactor forms, like the likewise known polymerization in batchwise operation or in a tubular reactor, as described, for example, in EP 445 619 A2 and DE 19 846 413 A1, a polymer gel which must be comminuted in a further process step, for example in a meat grinder, extruder or kneader. It is, however, also possible to produce spherical or differently shaped superabsorbent particles by suspension or emulsion polymerization, as described, for example, in EP 457 660 A1, or by spray or droplet polymerization processes, as described, for example, in EP 348 180 A1, EP 816 383 A1, WO 96/404 27 A1, U.S. Pat. No. 4,020,256, US 2002/0 193 546 A1, DE 35 19 013 A1, DE 10 2005 044 035 A1, WO 2007/093531 A1, WO 2008/086 976 A1 or WO 2009/027 356 A1. Likewise known are processes in which the monomer mixture is applied to a substrate, for example a nonwoven web, and polymerized, as described, for instance, in WO 02/94 328 A2 and WO 02/94 329 A1.

The polymer gel obtained from the aqueous solution polymerization and optional subsequent neutralization is then preferably dried with a belt drier until the residual moisture content is preferably from 0.5 to 15% by weight, more preferably from 1 to 10% by weight, most preferably from 2 to 8% by weight (see below for test method for the residual moisture or water content). In the case of too high a residual moisture content, the dried polymer gel has too low a glass transition temperature Tg and can be processed further only with difficulty. In the case of too low a residual moisture content, the dried polymer gel is too brittle and, in the subsequent comminution steps, undesirably large amounts of polymer particles with too low a particle size ("fines") are obtained. The solids content of the gel before drying is generally from 25 to 90% by weight, preferably from 30 to 80% by weight, more preferably from 35 to 70% by weight, most preferably from 40 to 60% by weight. Optionally, however, it is also possible to dry using a fluidized bed drier or a heatable mixer with a mechanical mixing unit, for example a paddle drier or a similar drier with mixing tools of different design. Optionally, the drier can be operated under nitrogen or another nonoxidizing inert gas or at least under reduced partial oxygen pressure in order to prevent oxidative yellowing processes. In general, however, even sufficient venting and removal of water vapor leads to an acceptable product. A very short drying time is generally advantageous with regard to color and product quality.

During the drying, the residual monomer content in the polymer particles is also reduced, and last residues of the initiator are destroyed.

Thereafter, the dried polymer gel is ground and classified, apparatus usable for the grinding typically including single- or multistage roll mills, preferably two- or three-stage roll mills, pin mills, hammer mills or vibratory mills. Oversize gel lumps which often still have not dried on the inside are elastomeric, lead to problems in the grinding and are preferably removed before the grinding, which can be done in a simple manner by wind sifting or by means of a screen ("protective screen" for the mill). In view of the mill used, the mesh size of the screen should be selected such that a minimum level of disruption resulting from oversize, elastomeric particles occurs.

Excessively large, insufficiently finely ground superabsorbent particles are perceptible as coarse particles in their predominant use, in hygiene products such as diapers; they also lower the mean initial swell rate of the superabsorbent. Both are undesired. Advantageously, coarse-grain polymer particles are therefore removed from the product. This is typically done by classification processes, for example wind sifting, or by screening through a screen with a mesh size of at most 1000 μm, preferably at most 900 μm, more preferably at most 850 μm and most preferably at most 800 μm. For example, screens of mesh size 700 μm, 650 μm or 600 μm are used. The coarse polymer particles ("oversize") removed may, for cost optimization, be sent back to the grinding and screening cycle or be processed further separately.

Polymer particles with too low a particle size lower the permeability (SFC). Advantageously, fine polymer particles are therefore also removed in this classification. This can, if screening is effected, conveniently be used through a screen of mesh size at most 300 μm, preferably at most 200 μm, more preferably at most 150 μm and most preferably at most 100 μm. The fine polymer particles ("undersize" or "fines") removed can, for cost optimization, be sent back as desired to the monomer stream, to the polymerizing gel or to the fully polymerized gel before the drying of the gel.

The mean particle size of the polymer particles removed as the product fraction is generally at least 200 μm, preferably at least 250 μm and more preferably at least 300 μm, and generally at most 600 μm and more preferably at most 500 μm. The proportion of particles with a particle size of at least 150 μm is generally at least 90% by weight, more preferably at least 95% by weight and most preferably at least 98% by weight. The proportion of particles with a particle size of at most 850 μm is generally at least 90% by weight, more preferably at least 95% by weight and most preferably at least 98% by weight.

In some other known production processes for superabsorbents, especially in suspension polymerization, spray polymerization or dropletization polymerization, the particle size distribution is defined by the selection of the process parameters. These processes directly give rise to particulate superabsorbents of the desired particle size, such that grinding and sieving steps can often be dispensed with. In some processes (especially in the case of spray or dropletization polymerization), it is often also possible for a dedicated drying step to be dispensed with.

The polymer thus prepared has superabsorbent properties and is covered by the term "superabsorbent". Its CRC is typically comparatively high, but its AUL or SFC comparatively low. A surface nonpostcrosslinked superabsorbent of this type is often referred to as "base polymer" to distinguish it from a surface postcrosslinked superabsorbent produced therefrom.

Suitable postcrosslinkers are compounds which comprise groups which can form bonds with at least two functional groups of the superabsorbent particles. In the case of the acrylic acid/sodium acrylate-based superabsorbents prevalent on the market, suitable surface postcrosslinkers are compounds which comprise groups which can form bonds with at least two carboxylate groups. Preferred postcrosslinkers are amide acetals or carbamates of the general formula (I)

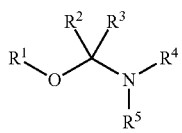
(I)

in which
$R^1$ is $C_1$-$C_{12}$-alkyl, $C_2$-$C_{12}$-hydroxyalkyl, $C_2$-$C_{12}$-alkenyl or $C_6$-$C_{12}$-aryl,
$R^2$ is X or $OR^6$,
$R^3$ is hydrogen, $C_1$-$C_{12}$-alkyl, $C_2$-$C_{12}$-hydroxyalkyl, $C_2$-$C_{12}$-alkenyl or $C_6$-$C_{12}$-aryl, or X,
$R^4$ is $C_1$-$C_{12}$-alkyl, $C_2$-$C_{12}$-hydroxyalkyl, $C_2$-$C_{12}$-alkenyl or $C_6$-$C_{12}$-aryl,
$R^5$ is hydrogen, $C_1$-$C_{12}$-alkyl, $C_2$-$C_{12}$-hydroxyalkyl, $C_2$-$C_{12}$-alkenyl, $C_1$-$C_{12}$-acyl or $C_6$-$C_{12}$-aryl,
$R^6$ is $C_1$-$C_{12}$-alkyl, $C_2$-$C_{12}$-hydroxyalkyl, $C_2$-$C_{12}$-alkenyl or $C_6$-$C_{12}$-aryl and
X is a carbonyl oxygen for the $R^2$ and $R^3$ radicals together, where $R^1$ and $R^4$ and/or $R^5$ and $R^6$ may be a bridged $C_2$-$C_6$-alkanediyl and where the abovementioned $R^1$ to $R^6$ radicals may also have a total of from one to two free valences and may be joined to at least one suitable base structure by these free valances,
or polyhydric alcohols, the polyhydric alcohol preferably having a molecular weight of less than 100 g/mol, preferably of less than 90 g/mol, more preferably of less than 80 g/mol, most preferably of less than 70 g/mol, per hydroxyl group, and no vicinal, geminal, secondary or tertiary hydroxyl groups, and polyhydric alcohols are either diols of the general formula (IIa)

$$HO-R^7-OH \quad (IIa)$$

in which $R^7$ is either an unbranched alkylene radical of the formula $-(CH_2)_n-$ where n is an integer from 3 to 20, preferably from 3 to 12, and both hydroxyl groups are terminal, or $R^7$ is an unbranched, branched or cyclic alkylene radical, or polyols of the general formula (IIb)

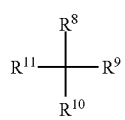
(IIb)

in which the $R^8$, $R^9$, $R^{10}$, $R^{11}$ radicals are each independently hydrogen, hydroxyl, hydroxymethyl, hydroxyethyloxymethyl, 1-hydroxyprop-2-yloxymethyl, 2-hydroxypropyloxymethyl, methyl, ethyl, n-propyl, isopropyl, n-butyl, n-pentyl, n-hexyl, 1,2-dihydroxy-ethyl, 2-hydroxyethyl, 3-hydroxypropyl or 4-hydroxybutyl, and a total of 2, 3 or 4, preferably 2 or 3, hydroxyl groups are present, and not more than one of the $R^8$, $R^9$, $R^{10}$, and $R^{11}$ radicals is hydroxyl, or cyclic carbonates of the general formula (III)

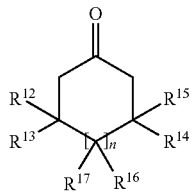
(III)

in which $R^{12}$, $R^{13}$, $R^{14}$, $R^{15}$, $R^{16}$ and $R^{17}$ are each independently hydrogen, methyl, ethyl, n-propyl, isopropyl, n-butyl, sec-butyl or isobutyl, and n is either 0 or 1, or bisoxazolines of the general formula (IV)

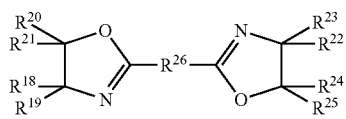
(IV)

in which $R^{18}$, $R^{19}$, $R^{20}$, $R^{21}$, $R^{22}$, $R^{23}$, $R^{24}$ and $R^{25}$ are each independently hydrogen, methyl, ethyl, n-propyl, isopropyl, n-butyl, sec-butyl or isobutyl, and $R^{26}$ is a single bond, a linear, branched or cyclic $C_2$-$C_{12}$-alkylene radical, or a polyalkoxydiyl radical which is formed from one to ten ethylene oxide and/or propylene oxide units, as possessed, for example, by polyglycoldicarboxylic acids.

Preferred postcrosslinkers of the general formula (I) are 2-oxazolidones such as 2-oxazolidone and N-(2-hydroxyethyl)-2-oxazolidone, N-methyl-2-oxazolidone, N-acyl-2-oxazolidones such as N-acetyl-2-oxazolidone, 2-oxotetrahydro-1,3-oxazine, bicyclic amide acetals such as 5-methyl-1-aza-4,6-dioxabicyclo[3.3.0]octane, 1-aza-4,6-dioxabicyclo[3.3.0]octane and 5-isopropyl-1-aza-4,6-dioxabicyclo[3.3.0]octane, bis-2-oxazolidones and poly-2-oxazolidones.

Particularly preferred postcrosslinkers of the general formula (I) are 2-oxazolidone, N-methyl-2-oxazolidone, N-(2-hydroxyethyl)-2-oxazolidone and N-hydroxypropyl-2-oxazolidone.

Preferred postcrosslinkers of the general formula (IIa) are 1,3-propanediol, 1,5-pentanediol, 1,6-hexanediol and 1,7-heptanediol. Further examples of postcrosslinkers of the formula (IIa) are 1,3-butanediol, 1,8-octanediol, 1,9-nonanediol and 1,10-decanediol.

The diols are preferably water-soluble, the diols of the general formula (IIa) being water-soluble at 23° C. to an extent of at least 30% by weight, preferably to an extent of at least 40% by weight, more preferably to an extent of at least 50% by weight, most preferably at least to an extent of 60% by weight, for example 1,3-propanediol and 1,7-heptanediol. Even more preferred are those postcrosslinkers which are liquid at 25° C.

Preferred postcrosslinkers of the general formula (IIb) are butane-1,2,3-triol, butane-1,2,4-triol, glycerol, trimethylolpropane, trimethylolethane, pentaerythritol, 1- to 3-tuply (per molecule) ethoxylated glycerol, trimethylolethane or trimethylolpropane and 1- to 3-tuply (per molecule) propoxylated glycerol, trimethylolethane or trimethylolpropane. Additionally preferred are 2-tuply ethoxylated or propoxylated neopentyl glycol. Particular preference is given to 2-tuply and 3-tuply ethoxylated glycerol, neopentyl glycol, 2-methyl-1, 3-propanediol and trimethylolpropane.

Preferred polyhydric alcohols (IIa) and (IIb) have, at 23° C., a viscosity of less than 3000 mPas, preferably less than 1500 mPas, preferentially less than 1000 mPas, more preferably less than 500 mPas, most preferably less than 300 mPas.

Particularly preferred postcrosslinkers of the general formula (III) are ethylene carbonate and propylene carbonate.

A particularly preferred postcrosslinker of the general formula (IV) is 2,2'-bis(2-oxazoline).

The preferred postcrosslinkers minimize side reactions and subsequent reactions which lead to volatile and hence malodorous compounds. The superabsorbents prepared with the preferred postcrosslinkers are therefore odor-neutral even in the moistened state.

It is possible to use an individual postcrosslinker from the above selection or any mixtures of different postcrosslinkers.

The postcrosslinker is generally used in an amount of at least 0.001% by weight, preferably of at least 0.02% by weight, more preferably of at least 0.05% by weight, and generally at most 2% by weight, preferably at most 1% by weight, more preferably at most 0.3% by weight, for example at most 0.15% by weight or at most 0.095% by weight, based in each case on the mass of the base polymer contacted therewith (for example of the sieve fraction in question).

The postcrosslinking is typically carried out in such a way that a solution of the postcrosslinker is sprayed onto the dried base polymer particles. After the spray application, the polymer particles coated with postcrosslinker are dried thermally, and the postcrosslinking reaction may take place either before or during the drying. If surface postcrosslinkers with polymerizable groups are used, the surface postcrosslinking can also be effected by means of free-radically induced polymerization of such groups by means of common free-radical formers or else by means of high-energy radiation, for example UV light. This can be done in parallel or instead of the use of postcrosslinkers which form covalent or ionic bonds to functional groups at the surface of the base polymer particles.

The spray application of the postcrosslinker solution is preferably carried out in mixers with moving mixing tools, such as screw mixers, disk mixers or paddle mixers, or mixers with other mixing tools. Particular preference is given, however, to vertical mixers. However, it is also possible to spray on the postcrosslinker solution in a fluidized bed. Suitable mixers are, for example, obtainable as Pflugschar® plowshare mixers from Gebr. Lödige Maschinenbau GmbH, Elsener-Strasse 7-9, 33102 Paderborn, Germany, or as Schugi® Flexomix® mixers, Vrieco-Nauta® mixers or Turbulizer® mixers from Hosokawa Micron BV, Gildenstraat 26, 7000 AB Doetinchem, the Netherlands.

The spray nozzles usable are not subject to any restriction. Suitable nozzles and atomization systems are described, for example, in the following references: Zerstäuben von Flüssigkeiten [Atomization of Liquids], Expert-Verlag, vol. 660, Reihe Kontakt & Studium, Thomas Richter (2004), and in Zerstäubungstechnik [Atomization Technology], Springer-Verlag, VDI-Reihe, Günter Wozniak (2002). It is possible to use mono- and polydisperse spray systems. Among the polydisperse systems, one-substance pressurized nozzles (jet- or lamellar-forming), rotational atomizers, two-substance atomizers, ultrasound atomizers and impingement nozzles are suitable. In the case of the two-substance atomizers, the liquid phase can be mixed with the gas phase either internally or externally. The spray profile of the nozzles is uncritical and may assume any desired form, for example a round jet, flat jet, wide angle round beam or circular ring spray profile. It is advantageous to use a nonoxidizing gas if two-substance atomizers are used, particular preference being given to nitrogen, argon or carbon dioxide. The liquid to be sprayed can be supplied to such nozzles under pressure. The liquid to be sprayed can be atomized by decompressing it in the die bore on attainment of a particular minimum velocity. In addition, it is also possible to use one-substance nozzles for the inventive purpose, for example slot dies or impingement chambers (full-cone nozzles) (for example from Düsen-Schlick GmbH, Germany, or from Spraying Systems Deutschland GmbH, Germany). Such nozzles are also described in EP 0 534 228 A1 and EP 1 191 051 A2.

The postcrosslinkers are typically used in the form of an aqueous solution. When exclusively water is used as the solvent, a surfactant or deagglomeration assistant is advantageously added to the postcrosslinker solution or actually to the base polymer. This improves the wetting performance and reduces the tendency to form lumps.

All anionic, cationic, nonionic and amphoteric surfactants are suitable as deagglomeration assistants, but preference is given to nonionic and amphoteric surfactants for skin compatible reasons. The surfactant may also comprise nitrogen. For example, sorbitan monoesters, such as sorbitan monococoate and sorbitan monolaurate, or ethoxylated variants thereof, for example Polysorbat 20®, are added. Further suitable deagglomeration assistants are the ethoxylated and alkoxylated derivatives of 2-propylheptanol, which are sold under the Lutensol XL® and Lutensol XP® brands (BASF SE, Carl-Bosch-Strasse 38, 67056 Ludwigshafen, Germany).

The deagglomeration assistant can be metered in separately or added to the postcrosslinker solution. Preference is given to simply adding the deagglomeration assistant to the postcrosslinker solution.

The amount of the deagglomeration assistant used, based on base polymer, is, for example, from 0 to 0.1% by weight, preferably from 0 to 0.01% by weight, more preferably from 0 to 0.002% by weight. The deagglomeration assistant is preferably metered in such that the surface tension of an aqueous extract of the swollen base polymer and/or of the swollen postcrosslinked water-absorbing polymer at 23° C. is at least 0.060 N/m, preferably at least 0.062 N/m, more preferably at least 0.065 N/m, and advantageously at most 0.072 N/m.

The aqueous postcrosslinker solution may, as well as the at least one postcrosslinker, also comprise a cosolvent. The content of nonaqueous solvent or total amount of solvent can be used to adjust the penetration depth of the postcrosslinker into the polymer particles. Industrially readily available cosolvents are C1-C6-alcohols such as methanol, ethanol, n-propanol, isopropanol, n-butanol, sec-butanol, tert-butanol or 2-methyl-1-propanol, C2-C5-diols such as ethylene glycol, 1,2-propylene glycol or 1,4-butanediol, ketones such as acetone, or carboxylic esters such as ethyl acetate. A disadvantage of some of these cosolvents is that they have typical intrinsic odors.

The cosolvent itself is ideally not a postcrosslinker under the reaction conditions. However, it may arise in the boundary case and depending on the residence time and temperature that the cosolvent contributes partly to crosslinking. This is the case especially when the postcrosslinker is relatively sluggish and therefore can also be its own cosolvent, as, for example, in the case of use of cyclic carbonates of the general formula (III), diols of the general formula (IIa) or polyols of the general formula (IIb). Such postcrosslinkers can be used in a mixture with more reactive postcrosslinkers or else in the function as a cosolvent, since the actual postcrosslinking reaction can then be carried out at lower temperatures and/or with shorter residence times than in the absence of the more reactive crosslinker. Since the cosolvent is used in relatively large amounts and also remains partly in the product, it must not be toxic.

Also suitable as cosolvents in the process according to the invention are the diols of the general formula (IIa), the polyols of the general formula (IIb), and the cyclic carbonates of the general formula (III). They fulfill this function in the presence of a reactive postcrosslinker of the general formula (I) and/or (IV) and/or of a di- or triglycidyl compound. Preferred cosolvents in the process according to the invention are, however, especially the diols of the general formula (IIa), especially when a reaction of the hydroxyl groups is hindered sterically by neighboring groups. Although such diols are also suitable in principle as postcrosslinkers, this requires significantly higher reaction temperatures or optionally higher use amounts than for sterically unhindered diols.

Particularly preferred combinations of low-reactivity postcrosslinker as a cosolvent and reactive postcrosslinker are combinations of preferred polyhydric alcohols, diols of the general formula (IIa) and polyols of the general formula (IIb), with amide acetals or carbamates of the general formula (I).

Suitable combinations are, for example, 2-oxazolidone/1,2-propanediol and N-(2-hydroxyethyl)-2-oxazolidone/1,2-propanediol, and also ethylene glycol diglycidyl ether/1,2-propanediol.

Very particularly preferred combinations are 2-oxazolidone/1,3-propanediol and N-(2-hydroxyethyl)-2-oxazolidone/1,3-propanediol.

Further preferred combinations are those with ethylene glycol diglycidyl ether or glyceryl di- or triglycidyl ether with the following solvents, cosolvents or cocrosslinkers: isopropanol, 1,3-propanediol, 1,2-propylene glycol or mixtures thereof.

Further preferred combinations are those with 2-oxazolidone or (2-hydroxyethyl)-2-oxazolidone in the following solvents, cosolvents or cocrosslinkers: isopropanol, 1,3-propanediol, 1,2-propylene glycol, ethylene carbonate, propylene carbonate or mixtures thereof.

Frequently, the concentration of the cosolvent in the aqueous postcrosslinker solution is from 15 to 50% by weight, preferably from 15 to 40% by weight, more preferably from 20 to 35% by weight, based on the postcrosslinker solution. In the case of cosolvents of only limited water miscibility, the aqueous postcrosslinker solution will advantageously be adjusted such that only one phase is present, optionally by lowering the concentration of the cosolvent.

In a preferred embodiment, no cosolvent is used. The postcrosslinker is then employed only as a solution in water, optionally with addition of a deagglomeration assistant.

The concentration of the at least one postcrosslinker in the aqueous postcrosslinker solution is typically from 1 to 20% by weight, preferably from 1.5 to 10% by weight, more preferably from 2 to 5% by weight, based on the postcrosslinker solution.

The total amount of the postcrosslinker solution based on base polymer is typically from 0.3 to 15% by weight, preferably from 2 to 6% by weight.

The actual surface postcrosslinking by reaction of the surface postcrosslinker with functional groups at the surface of the base polymer particles is usually carried out by heating the base polymer wetted with surface postcrosslinker solution, typically referred to as "drying" (but not to be confused with the above-described drying of the polymer gel from the polymerization, in which typically very much more liquid has to be removed). The drying can be effected in the mixer itself, by heating the jacket, by means of heat exchange surfaces or by blowing in warm gases. Simultaneous admixing of the superabsorbent with surface postcrosslinker and drying can be effected, for example, in a fluidized bed drier. The drying is, however, usually carried out in a downstream drier, for example a tray drier, a rotary tube oven, a paddle or disk drier or a heatable screw. Suitable driers are, for example, obtainable as Solidair® or Torusdisc® driers from Bepex International LLC, 333 N.E. Taft Street, Minneapolis, Minn. 55413, U.S.A., or as paddle driers or else as fluidized bed driers from Nara Machinery Co., Ltd., European Branch, Europaallee 46, 50226 Frechen, Germany.

It is possible to heat the polymer particles by means of contact surfaces in a downstream drier for the purpose of drying and performing the surface postcrosslinking, or by means of warm inert gas supply, or by means of a mixture of one or more inert gases with steam, or only with steam alone. In the case of supply of the heat by means of contact surfaces, it is possible to perform the reaction under inert gas at slightly or completely reduced pressure. In the case of use of steam for direct heating of the polymer particles, it is desirable in accordance with the invention to operate the drier under standard pressure or elevated pressure. In this case, it may be advisable to split up the postcrosslinking step into a heating step with steam and a reaction step under inert gas but without steam. This can be achieved in one or more apparatuses. According to the invention, the polymer particles can be heated with steam as early as in the postcrosslinking mixer. The base polymer used may still have a temperature of from 10 to 120° C. from preceding process steps; the postcrosslinker solution may have a temperature of from 0 to 70° C. In particular, the postcrosslinker solution can be heated to reduce the viscosity.

Preferred drying temperatures are in the range from 100 to 250° C., preferably from 120 to 220° C., more preferably from 130 to 210° C., most preferably from 150 to 200° C. The preferred residence time at this temperature in the reaction mixer or drier is preferably at least 10 minutes, more preferably at least 20 minutes, most preferably at least 30 minutes, and typically at most 60 minutes. Typically, the drying is conducted such that the superabsorbent has a residual moisture content of generally at least 0.1% by weight, preferably at least 0.2% by weight and most preferably at least 0.5% by weight, and generally at most 15% by weight, preferably at most 10% by weight and more preferably at most 8% by weight.

The postcrosslinking may take place under standard atmospheric conditions. "Standard atmospheric conditions" means that no technical precautions are taken in order to reduce the partial pressure of oxidizing gases, such as that of atmospheric oxygen, in the apparatus in which the postcrosslinking reaction predominantly takes place (the "postcrosslinking reactor", typically the drier). However, preference is given to performing the postcrosslinking reaction under reduced partial pressure of oxidizing gases. Oxidizing gases are substances which, at 23° C., have a vapor pressure of at least 1013 mbar and act as oxidizing agents in combustion processes, for example oxygen, nitrogen oxide and nitrogen dioxide, especially oxygen. The partial pressure of oxidizing gases is preferably less than 140 mbar, preferably less than 100 mbar, more preferably less than 50 mbar, most preferably less than 10 mbar. When the thermal postcrosslinking is carried out at ambient pressure, i.e. at a total pressure around 1013 mbar, the total partial pressure of the oxidizing gases is determined by their proportion by volume. The proportion of the oxidizing gases is preferably less than 14% by volume, preferably less than 10% by volume, more preferably less than 5% by volume, most preferably less than 1% by volume.

The postcrosslinking can be carried out under reduced pressure, i.e. at a total pressure of less than 1013 mbar. The total pressure is typically less than 670 mbar, preferably less than 480 mbar, more preferably less than 300 mbar, most preferably less than 200 mbar. When drying and postcrosslinking are carried out under air with an oxygen content of 20.8% by volume, the partial oxygen pressures corresponding to the abovementioned total pressures are 139 mbar (670 mbar), 100 mbar (480 mbar), 62 mbar (300 mbar) and 42 mbar (200 mbar), the particular total pressures being in the brackets. Another means of lowering the partial pressure of oxidizing gases is the introduction of nonoxidizing gases, especially inert gases, into the apparatus used for postcrosslinking. Suitable inert gases are substances which are present in gaseous form in the postcrosslinking drier at the postcrosslinking temperature and the given pressure and do not have an oxidizing action on the constituents of the drying polymer particles under these conditions, for example nitrogen, carbon dioxide, argon, steam, preference being given to nitrogen. The amount of inert gas is generally from 0.0001 to 10 $m^3$, preferably from 0.001 to 5 $m^3$, more preferably from 0.005 to 1 $m^3$ and most preferably from 0.005 to 0.1 $m^3$, based on 1 kg of superabsorbent.

In the process according to the invention, the inert gas, if it does not comprise steam, can be blown into the postcrosslinking drier via nozzles; however, particular preference is given to adding the inert gas to the polymer particle stream via nozzles actually within or just upstream of the mixer, by admixing the superabsorbent with surface postcrosslinker.

It will be appreciated that vapors of cosolvents removed from the drier can be condensed again outside the drier and optionally recycled.

In a preferred embodiment of the present invention, polyvalent cations are applied to the particle surface in addition to the postcrosslinkers before, during or after the postcrosslinking. This is in principle a further surface postcrosslinking by means of ionic noncovalent bonds, but is occasionally also referred to as "complexation" with the metal ions in question or simply as "coating" with the substances in question (the "complexing agent").

This application of polyvalent cations is effected by spray application of solutions of di- or polyvalent cations, usually di-, tri- or tetravalent metal cations, but also polyvalent cations such as polymers formed, in a formal sense, entirely or partly from vinylamine monomers, such as partly or fully hydrolyzed polyvinylamide (so-called "polyvinylamine"), whose amine groups are always—even at very high pH values—present partly in protonated form to give ammonium groups. Examples of usable divalent metal cations are especially the divalent cations of metals of groups 2 (especially Mg, Ca, Sr, Ba), 7 (especially Mn), 8 (especially Fe), 9 (especially Co), 10 (especially Ni), 11 (especially Cu) and 12 (especially Zn) of the Periodic Table of the Elements. Examples of usable trivalent metal cations are especially the trivalent cations of metals of groups 3 including the lanthanides (especially Sc, Y, La, Ce), 8 (especially Fe), 11 (especially Au) and 13 (especially Al) of the Periodic Table of the Elements. Examples of usable tetravalent cations are especially the tetravalent cations of metals from the lanthanides (especially Ce) and group 4 (especially Ti, Zr, Hf) of the Periodic Table of the Elements. The metal cations can be used either alone or in a mixture with one another. Particular preference is given to the use of trivalent metal cations. Very particular preference is given to the use of aluminum cations.

Among the metal cations mentioned, suitable metal salts are all of those which possess sufficient solubility in the solvent to be used. Particularly suitable metal salts are those with weakly complexing anions, for example chloride, nitrate and sulfate, hydrogen-sulfate, carbonate, hydrogencarbonate, nitrate, phosphate, hydrogenphosphate, or dihydrogenphosphate. Preference is given to salts of mono- and dicarboxylic acids, hydroxy acids, keto acids and amino acids, or basic salts. Examples are acetates, propionates, tartrates, maleates, citrates, lactates, malates and succinates. Equally preferred is the use of hydroxides. Particular preference is given to the use of 2-hydroxycarbonic salts such as citrates and lactates. Examples of particularly preferred metal salts are alkali metal and alkaline earth metal aluminates and hydrates thereof, for instance sodium aluminate and hydrates thereof, aluminum acetate, aluminum propionate, aluminum citrate and aluminum lactate.

The cations and salts mentioned may be used in pure form or as a mixture of different cations or salts. The salts of the di- and/or trivalent metal cation used may comprise further secondary constituents such as still unneutralized carboxylic acid and/or alkali metal salts of the neutralized carboxylic acid. Preferred alkali metal salts are those of sodium and potassium, and those of ammonium. They are typically used in the form of an aqueous solution which is obtained by dissolving the solid salts in water, or is preferably obtained directly as such, which avoids any drying and purification steps. Advantageously, it is also possible to use the hydrates of the salts mentioned, which often dissolve more rapidly in water than the anhydrous salts.

The amount of metal salt used is generally at least 0.001% by weight, preferably at least 0.01% by weight and more preferably at least 0.1% by weight, for example at least 0.4% by weight, and generally at most 5% by weight, preferably at most 2.5% by weight and more preferably at most 1% by weight, for example at most 0.7% by weight, based in each case on the mass of the base polymer.

The salt of the trivalent metal cation can be used in the form of a solution or suspension. The solvents used for the metal salts may be water, alcohols, DMF, DMSO, and mixtures of these components. Particular preference is given to water and water/alcohol mixtures, for example water/methanol, water/1,2-propanediol and water/1,3-propanediol.

The base polymer is treated with a solution of a divalent or polyvalent cation in the same manner as that with surface postcrosslinker, including the drying step. Surface postcrosslinker and polyvalent cation can be sprayed on in a combined solution or as separate solutions. The spray application of the metal salt solution to the superabsorbent particles can be effected either before or after the surface postcrosslinking. In a particularly preferred process, the spray application of the metal salt solution is effected in the same step as the spray application of the crosslinker solution, both solutions being sprayed on separately and successively or simultaneously through two nozzles, or crosslinker and metal salt solution may be sprayed on together through one nozzle.

If, after the surface postcrosslinking and/or treatment with complexing agent, a drying step is carried out, it is advantageous but not absolutely necessary to cool the product after the drying step. The cooling can be effected continuously or batchwise; to this end, the product is conveniently conveyed continuously into a cooler connected downstream of the drier. To this end, it is possible to use any apparatus known for removal of heat from pulverulent solids, especially any apparatus mentioned above as a drying apparatus, provided that it is not charged with a heating medium but rather with a cooling medium, for instance with cooling water, such that no heat is introduced into the superabsorbent via the walls and, according to the construction, also via the stirrer units or other heat exchange surfaces, but rather removed therefrom. Preference is given to the use of coolers in which the product is moved, i.e. cooled mixers, for example paddle coolers or disk coolers. The superabsorbent can also be cooled in a fluidized bed by blowing in a cooled gas such as cold air. The cooling conditions are established such that a superabsorbent with the temperature desired for further processing is obtained. Typically, a mean residence time in the cooler of generally at least 1 minute, preferably at least 3 minutes and more preferably at least 5 minutes, and generally at most 6 hours, preferably at most 2 hours and more preferably at most 1 hour, is established, and the cooling performance is such that the resulting product has a temperature of generally at least 0° C., preferably at least 10° C. and more preferably at least 20° C., and generally at most 100° C., preferably at most 80° C. and more preferably at most 60° C.

The surface postcrosslinked superabsorbent is optionally ground and/or screened in a customary manner. Grinding is typically not required here, but screening-off of agglomerates or fines formed is usually appropriate to establish the desired particle size distribution of the product. Agglomerates and fines are either discarded or preferably recycled into the process in a known manner at a suitable point; agglomerates after comminution. The particle sizes desired for surface postcrosslinked superabsorbents are the same as for base polymers.

The inventive superabsorbents are optionally and preferably provided with further additives which stabilize against discoloration. These additives can be added at any suitable time. They are preferably added to the superabsorbent, i.e. they are not added to the monomer mixture or to a monomer, but rather only once crosslinked polymer is present, i.e. no earlier than during the polymerization. They can be added, for example, during the polymerization, during a surface postcrosslinking step or after the surface postcrosslinking.

Known stabilizers against discoloration of this kind are, for example, derivatives of sulfinic acid. Particularly suitable derivatives of sulfinic acid are, for example, compounds of the following formula (V):

in which

M is a hydrogen atom, an ammonium ion, a monovalent metal ion or one equivalent of a divalent metal ion of groups 1, 2, 8, 9, 10, 12 or 14 of the Periodic Table of the Elements;

$R^{27}$ is OH or $NR^{30}R^{31}$ where $R^{30}$ and $R^{31}$ are each independently H or $C_1$-$C_6$-alkyl;

$R^{28}$ is H or an alkyl, alkenyl, cycloalkyl or aryl group, where this group optionally has 1, 2 or 3 substituents which are each independently selected from $C_1$-$C_6$-alkyl, OH, O—$C_1$-$C_6$-alkyl, halogen and $CF_3$; and $R^{29}$ is COOM, $SO_3M$, $COR^{30}$, $CONR^{30}R^{31}$ or $COOR^{30}$, where M, $R^{30}$ and $R^{31}$ are each as defined above or, when $R^{28}$ is aryl which is optionally substituted as specified above, are also H, salts thereof or mixtures of such compounds and/or salts thereof.

In the above formula (V), alkyl represents straight-chain or branched alkyl groups which have preferably 1-6 and especially 1-4 carbon atoms. Examples of alkyl groups are methyl, ethyl, n-propyl, isopropyl, n-butyl, t-butyl, n-hexyl, etc. The same applies to the alkyl groups in O-alkyl. Alkenyl represents straight-chain or branched alkenyl groups which have preferably 3-8 carbon atoms, especially 3-6 carbon atoms. A preferred alkenyl group is the allyl group. Cycloalkyl is especially $C_1$-$C_6$-cycloalkyl, particular preference being given to cyclopentyl and cyclohexyl. Aryl (including in aralkyl) is preferably phenyl or naphthyl. When the aryl radical is a phenyl group and is substituted, it preferably has two substituents. These are present especially in the 2 and/or 4 position.

Halogen is F, Cl, Br and I, preferably Cl and Br.

M is preferably an ammonium ion, alkali metal ion or one equivalent of an alkaline earth metal or zinc ion. Suitable alkali metal ions are especially sodium and potassium ions; suitable alkaline earth metal ions are in particular magnesium, strontium and calcium ions.

$R^{27}$ is preferably a hydroxyl or amino group.

$R^{28}$ is preferably a hydrogen atom or an alkyl or aryl group which may be substituted as above. It preferably has one or two hydroxyl and/or alkoxy substituents.

$R^{29}$ is preferably either COOM or $COOR^{30}$ (M and $R^{30}$ are each defined as specified above) or, when $R^{27}$ is aryl which may be substituted as specified above, is also a hydrogen atom.

In a preferred embodiment, the superabsorbent comprises compounds of the above formula in which M is an alkali metal ion or one equivalent of an alkaline earth metal or zinc ion; $R^{27}$ is a hydroxyl or amino group; $R^{28}$ is H or alkyl and $R^{29}$ is COOM or $COOR^{30}$, where, when $R^{29}$ is COOM, M in this COOM radical is H, an alkali metal ion or one equivalent of an alkaline earth metal ion, and, when $R^{29}$ is $COOR^{30}$, $R^{30}$ is $C_1$-$C_6$-alkyl.

In a further preferred embodiment, the superabsorbent comprises compounds of the above formula in which M is an alkali metal ion or one equivalent of an alkaline earth metal or zinc ion; $R^{27}$ is a hydroxyl or amino group; $R^{28}$ is aryl which is optionally substituted as specified above, especially hydroxyphenyl or $C_1$-$C_4$-alkoxyphenyl; and $R^{29}$ is a hydrogen atom.

Groups 1 (H, Li, Na, K, Rb, Cs, Fr), 2 (Be, Mg, Ca, Sr, Ba, Ra), 8 (Fe, Ru, Os), 9 (Co, Rh, Ir), 10 (Ni, Pd, Pt), 12 (Zn, Cd, Hg) and 14 (C, Si, Ge, Sn, Pb) of the Periodic Table of the Elements in the current IUPAC numbering (International Union of Pure and Applied Chemistry, 104 T.W. Alexander Drive, Building 19, Research Triangle Park, N.C. 27709, U.S.A., www.iupac.org), the international organization responsible for nomenclature in the field of chemistry, correspond to groups Ia, IIa, IIb, IVa and VIIIb in the numbering used by CAS (Chemical Abstracts Service, 2540 Olentangy River Road, Columbus, Ohio 43202, U.S.A., www.cas.org).

The sulfinic acid derivatives of the above formula can be used in pure form, but optionally also in the mixture with the sulfite of the corresponding metal ion and of the corresponding sulfonic acid which results in a customary manner from the preparation of such compounds. The preparation of such sulfinic acid derivatives of the above formula is known and is described, for example, in WO 99/18 067 A1. They are also conventional commercial products and are available, for example, in the form of mixtures of the sodium salt of 2-hydroxy-2-sulfinatoacetic acid, the disodium salt of 2-hydroxy-2-sulfonatoacetic acid and sodium bisulfite from L. Brüggemann KG (Salzstrasse 131, 74076 Heilbronn, Germany, www.brueggemann.com) under the names BRÜGGOLIT® FF6M or BRÜGGOLIT® FF7, or alternatively BRUGGOLITE® FF6M or BRUGGOLITE® FF7.

Further usable stabilizers against discoloration are sterically hindered phenols. Sterically hindered phenols are understood to mean phenols which bear a singly or doubly branched substituent, preferably a doubly branched substituent, at least in the 2 position and optionally also in the 6 position on the phenyl ring. Branched substituents are understood to mean substituents which bear, on the atom bonded to the phenyl ring of the phenol, apart from the carbon atom of the phenyl ring to which they are bonded, at least two radicals other than hydrogen. However, sterically hindered phenols are also those which bear a sterically demanding unbranched substituent at least in the 2 position and optionally also in the 6 position. This is understood to mean substituents which comprise at least 6, preferably at least 8 and more preferably at least 12 atoms other than hydrogen, but, on the atom bonded to the phenyl ring of the phenol, apart from the carbon atom of the phenyl ring to which they are bonded, bear only one radical other than hydrogen. The simplest examples of singly branched substituents are secondary alkyl radicals such as 2-propyl, 2-butyl, 2-pentyl, 3-pentyl, ethylhexyl, or cycloalkyl radicals such as cyclobutyl, cyclopentyl, cyclohexyl, or aromatic radicals such as phenyl. The simplest examples of doubly branched substituents are tertiary alkyl radicals such as tert-butyl, tert-pentyl or norbornyl. The simplest examples of unbranched radicals are hexyl, heptyl, octyl, nonyl, decyl, undecyl and dodecyl, but also neopentyl, neohexyl or dodecylthiomethyl. All these radicals may, however, also themselves be substituted or comprise atoms other than carbon and hydrogen. The phenyl ring of the phenol may, in addition to the substituent in the 2 position and optionally in the 6 position, also optionally bear further substituents. Examples of preferred sterically hindered phenols are 2-tert-butylphenol, 2,6-di-tert-butylphenol, 2,6-di-tert-butyl-4-methylphenol (also referred to as 2,6-di-tert-butyl-para-cresol or 3,5-di-tert-butyl-4-hydroxytoluene), 3,5-di-tert-butyl-4-hydroxyphenylacetic acid, 3,5-di-tert-butyl-4-hydroxyphenylpropionic acid and the esters of these acids with alcohols and polyols, for example the mono- or polyesters thereof with glycol, glycerol, 1,2- or 1,3-propanediol, trimethylolpropane or pentaerythritol, for instance pentaerythrityl tetrakis(3-(3,5-di-tert-butyl-4-hydroxyphenyl)propionate) or octadecyl 3,5-di-tert-butyl-4-hydroxyphenyl)propionate, 4,4-thiobis (6-tert-butyl-meta-cresol), 4,6-bis(dodecylthiomethyl)-ortho-cresol, 3,3',3'',5,5',5''-hexa-tert-butyl-$\alpha,\alpha',\alpha''$-(mesitylene-2,4,6-triyl)tri-para-cresol (alternative name for 2,4,6-tri [(4-hydroxy-3,5-di-tert-butylphenyl)methyl]nesitylene, CAS No. 1709-70-2, obtainable from Ciba Specialty Chemicals, Basle, Switzerland AG (now BASF Switzerland AG), under the Irganox® 1330 brand), N,N-hexane-1,3-diylbis(3-(3,5-di-tert-butyl-4-hydroxphenylpropionamide)), 2,2'-ethylidenebis[4,6-bis(1,1-dimethylethyl)phenol] and ethylenebis(oxyethylene)bis-3-(5-tert-butyl-4-hydroxy-m-tolyl) propionate) (CAS No. 36443-68-2, obtainable from Ciba Specialty Chemicals, Basle, Switzerland AG (now BASF Switzerland AG), under the Irganox® 245 brand).

Further examples of stabilizers against discoloration are especially reducing substances. Among these, solid or dissolved salts and esters of phosphinic acid ($H_3PO_2$), and this acid itself, are preferred. For example, all phosphinates (also referred to as hypophosphites) of the alkali metals, including that of ammonium, and of the alkaline earth metals, are suitable. Suitable examples are also aqueous solutions of phosphinic acid which comprise phosphinate ions and at least one cation selected from sodium, potassium, ammonium, calcium, strontium, aluminum, magnesium. Equally preferred are esters of phosphinic acid or salts of esters of phosphinic acid. One example thereof is sodium diphenylphosphinate.

Likewise preferred are solid or dissolved salts and esters of phosphonic acid ($HP(O)(OH)_2$) and phosphorous acid ($H_3PO_3$), and also phosphonic acid itself. Phosphonic acid is tautomeric with phosphorous acid; the latter does not exist as the free acid. True derivatives of phosphorous acid are solely the triesters thereof, which are typically referred to as phosphites. The derivatives of tautomeric phosphonic acid are typically referred to as phosphonates. For example, all primary and secondary phosphonates of the alkali metals, including those of ammonium, and of the alkaline earth metals, are suitable. Suitable examples are also aqueous solutions of phosphonic acid which comprise primary and/or secondary phosphonate ions and at least one cation selected from sodium, potassium, calcium, strontium. Examples of suitable phosphites or phosphonates are calcium bis[monoethyl(3,5-di-tert-butyl-4-hydroxybenzyl)phosphonate], tris(2,4-di-tert-butylphenyl)phosphite, 3,9-bis(octadecyl-oxy)-2,4,8,10-tetraoxa-3,9-diphosphaspiro[5.5]undecane and bis(2,4-di-tert-butyl-phenyl)pentaerythrityl diphosphite. Stabilizers may at the same time be phosphonates or phosphites and sterically hindered phenols.

The inventive superabsorbent is optionally admixed with at least one inorganic water-insoluble particulate solid. In principle, any inorganic water-insoluble powder is suitable for that purpose. Examples are generally solid, chemically inert (i.e. nondisruptive in the superabsorbent) substances such as oxides, oxide hydroxides, hydroxides, sulfates, carbonates, zeolites, inorganic pigments, minerals or clays. Examples are sulfates such as magnesium sulfate or barium sulfate, carbonates such as calcium carbonate, magnesium carbonate or dolomite, silicates such as calcium silicate or magnesium silicate, carbides such as perlite or silicon carbide, diatomaceous earth or fly ash.

Suitable oxides are the metal oxides of groups 2 to 14 of the Periodic Table of the Elements, including the lanthanides and actinides. Examples of particularly suitable oxides are magnesium oxide, calcium oxide, strontium oxide, barium oxide, titanium dioxide, zirconium dioxide, vanadium oxide, chromium oxide, molybdenum oxide, tungsten oxide, manganese dioxide, iron oxide, cobalt oxide, nickel oxide, copper oxide, zinc oxide, boron oxide, aluminum oxide, silicon dioxide, tin oxide, lead oxide, lanthanum oxide or cerium oxide. For clarity: the use of a trivial name for metal oxides is not supposed to be a statement about the valency of the metal and the stoichiometry of the oxide. If an element forms more than one oxide, all are generally suitable. In the individual case, the oxide is selected according to considerations specific to the individual case, for example according to cost, toxicity, stability or color. Examples of particularly suitable oxides are titanium dioxide, especially in the anatase or rutile polymorphs, precipitated silicon dioxide or silicon dioxide produced by pyrolysis.

Clays are silicates or aluminosilicates, which are typically obtained by mining of natural sediments and occasionally also the further processing thereof. However, some clays are produced synthetically.

It is also possible to use mixtures of these substances.

The inorganic water-insoluble solid is particulate; it is in pulverulent form. The mean particle size is typically in the region of at least 0.001 µm, preferably at least 0.002 µm, more preferably of at least 0.005 µm and most preferably of at least 0.01 µm, and generally of at most 500 µm, preferably at most 200 µm, more preferably at most 100 µm and most preferably of at most 50 µm. The particles may themselves be aggregates or agglomerates of smaller primary particles. The particle size can be determined by means of sieve analysis, but a simpler and therefore preferred method is the determination of the particle size by means of laser diffraction technology.

These processes are well known and are conducted routinely on suitable and commercially available equipment.

The aforementioned stabilizers against discoloration and the inorganic water-insoluble particulate solid are, when they are added, added in amounts of in each case generally at least 0.0001% by weight, preferably at least 0.001% by weight and more preferably at least 0.025% by weight, and generally at most 3% by weight, preferably at most 2% by weight and more preferably at most 0.5% by weight, based in each case on the total weight of the inventive superabsorbent. In general, in the case of the inventive superabsorbent comprising alkaline earth metal salt, a smaller amount of known stabilizers against discoloration is needed than without alkaline earth metal salt.

Superabsorbents can be mixed with stabilizers against discoloration and the inorganic water-insoluble particulate solid by any known mixing process. Stabilizers against discoloration and the inorganic water-insoluble particulate solid can be mixed in in substance, as a solution or as a suspension in a solvent or suspension medium; owing to the easier homogeneous distribution, they are preferably mixed in as a solution or suspension. This does not necessarily produce a physical mixture separable in a simple manner by mechanical measures. The additives may quite possibly enter into a more definite bond with the superabsorbent, for example in the form of a comparatively firmly adhering surface layer or in the form of particles adhering firmly to the surface of the superabsorbent particles. The mixing of the additives into the known superabsorbent can quite possibly also be understood and referred to as "coating".

If a solution or suspension is used for coating, the solvent or suspension medium used is a solvent or suspension medium which is chemically compatible both with the superabsorbent and with the additive, i.e. does not enter into any undesired chemical reactions therewith. Typically, water or an organic solvent is used, for example an alcohol or polyol, or mixtures thereof. Examples of suitable solvents or suspension media are water, isopropanol/water, 1,3-propanediol/water and propylene glycol/water, where the mass mixing ratio is preferably from 20:80 to 40:60. A surfactant can be added to the solution or suspension.

The additive is generally mixed with the superabsorbent in exactly the same way as the solution or suspension which comprises a surface postcrosslinker and is applied to the superabsorbent for surface postcrosslinking, as described below. The additive can be applied as a constituent of the solution applied for surface postcrosslinking or of one of the components thereof to an (as yet) nonpostcrosslinked superabsorbent (a "base polymer"), i.e. the additive is added to the solution of the surface postcrosslinker or to one of the components thereof. The superabsorbent coated with surface postcrosslinker and additive then passes through the further process steps required for surface postcrosslinking, for example a thermally induced reaction of the surface postcrosslinker with the superabsorbent. This process is comparatively simple and economically viable.

If ultrahigh stability to discoloration is essential, the additive is preferably applied in a dedicated process step after the surface postcrosslinking. If the additive is applied in the form of a solution or suspension, the application to the already surface postcrosslinked superabsorbent is effected in the same way as the application of the surface postcrosslinker to the base polymer. Usually, but not necessarily, this is followed, just like in the surface postcrosslinking step, by heating, in order to dry the superabsorbent again. The temperature established in this drying step is then, however, generally at most 110° C., preferably at most 100° C. and more preferably at most 90° C., in order to prevent undesired reactions of the additive. The temperature is adjusted such that, in view of the residence time in the drying unit, the desired water content of the superabsorbent is achieved. It is also entirely possible and convenient to add the additive individually or together with other customary assistants, for example antidusting agents, anticaking agents or water to remoisten the superabsorbent, as described below for these assistants, for example in a cooler connected downstream of the surface postcrosslinking step. The temperature of the polymer particles in this case is between 0° C. and 190° C., preferably less than 160° C., more preferably less than 130° C., even more preferably less than 100° C. and most preferably less than 70° C. The polymer particles are optionally cooled rapidly after coating to temperatures below any decomposition temperature of the additive.

It is optionally possible to additionally apply to the surface of the superabsorbent particles, whether unpostcrosslinked or postcrosslinked, in any process step of the preparation process, if required, all known coatings, such as film-forming polymers, thermoplastic polymers, dendrimers, polycationic polymers (for example polyvinylamine, polyethyleneimine or polyallylamine), or all water-soluble mono- or polyvalent metal salts known to those skilled in the art, for example aluminum sulfate, sodium salts, potassium salts, zirconium salts or iron salts. Examples of useful alkali metal salts are sodium and potassium sulfate, and sodium and potassium lactates, citrates and sorbates. This allows additional effects, for example a reduced caking tendency of the end product or of the intermediate in the particular process step of the production process, improved processing properties or a further enhanced saline flow conductivity (SFC), to be achieved. When additives are used and sprayed on in the form of dispersions, they are preferably used as aqueous dispersions, and preference is given to additionally applying an antidusting agent to fix the additive on the surface of the superabsorbent. The antidusting agent is then either added directly to the dispersion of the inorganic pulverulent additive; optionally, it can also be added as a separate solution before, during or after the application of the inorganic pulverulent additive by spray application. Most preferred is the simultaneous spray application of postcrosslinker, antidusting agent and pulverulent inorganic additive in the postcrosslinking step. In a further preferred process variant, the antidusting agent is, however, added separately in the cooler, for example by spray application from above, below or from the side. Particularly suitable antidusting agents which can also serve to fix pulverulent inorganic additives on the surface of the water-absorbing polymer particles are polyethylene glycols with a molecular weight of from 400 to 20 000 g/mol, polyglycerol, 3- to 100-tuply ethoxylated polyols such as trimethylolpropane, glycerol, sorbitol and neopentyl glycol. Particularly suitable are 7- to 20-tuply ethoxylated glycerol or trimethylolpropane, for example Polyol TP 70® (Perstorp, Sweden). The latter have, more particularly, the advantage that they lower the surface tension of an aqueous extract of the water-absorbing polymer particles only insignificantly.

It is equally possible to adjust the inventive superabsorbent to a desired water content by adding water.

All coatings, solids, additives and assistants can each be added in separate process steps, but the most convenient method is usually to add them—if they are not added during the admixing of the base polymer with surface postcrosslinkers—to the superabsorbent in the cooler, for instance by spray application of a solution or addition in finely divided solid form or in liquid form.

The inventive superabsorbents generally have a centrifuge retention capacity (CRC, for test method see below) of at least 5 g/g, preferably of at least 10 g/g and more preferably of at least 20 g/g. It is typically not more than 40 g/g.

The inventive superabsorbents have, when they are surface postcrosslinked, typically an absorption under pressure (AUL0.7 psi, see below for test method) of at least 18 g/g, preferably at least 20 g/g, preferentially at least 22 g/g, and typically not more than 30 g/g.

The inventive superabsorbents additionally typically have a saline flow conductivity (SFC, see below for test method) of at least $10 \times 10^{-7}$ cm$^3$s/g, preferably at least $30 \times 10^{-7}$ cm$^3$s/g, preferentially at least $40 \times 10^{-7}$ cm$^3$s/g, and typically not more than $1000 \times 10^{-7}$ cm$^3$s/g.

The L value of the superabsorbent (CIE color number) is, in the unstored state, typically at least 75, preferably at least 80, more preferably at least 85, and at most 100.

The a value of the superabsorbent (CIE color number) is, in the unstored state, typically from −2.5 to +2.5, preferably from −2.0 to +2.0, more preferably from −1.5 to +1.5.

The b value of the superabsorbent (CIE color number) in the unstored state is typically from 0 to 12, preferably from 2 to 11.

After the relatively high-stress aging test described below, the inventive superabsorbent, after analysis for the L and a values, has only slightly worsened results compared in the unstored state, more particularly compared to b values of preferably not more than 13, more preferably not more than 12. A b value above 12 is critical in feminine hygiene articles and ultrathin diapers; a b value of more than 15 is also critical even in conventional diapers, since this discoloration can be perceived by the consumer on use.

The present invention further provides hygiene articles comprising inventive superabsorbents, preferably ultrathin diapers, comprising an absorbent layer consisting of from 50 to 100% by weight, preferably from 60 to 100% by weight, preferentially from 70 to 100% by weight, more preferably from 80 to 100% by weight, most preferably from 90 to 100% by weight, of inventive superabsorbents, excluding, of course, the shell of the absorbent layer.

The inventive superabsorbents are also very particularly advantageous for production of laminates and composite structures, as described, for example, in US 2003/0181115 and US 2004/0019342. In addition to the hotmelt adhesives described in both documents for production of such novel absorbent structures and especially to the fibers composed of hotmelt adhesives which are described in US 2003/0181115 and to which the superabsorbent particles are bonded, the inventive superabsorbents are also suitable for producing entirely analogous structures using UV-crosslinkable hotmelt adhesives, which are sold, for example, as AC Resin® (BASF SE, Germany). These UV-crosslinkable hotmelt adhesives have the advantage of being processable even at from 120 to 140° C.; they are therefore better compatible with many thermoplastic substrates. A further significant advantage is that UV-crosslinkable hotmelt adhesives are toxicologically entirely safe and also do not cause any vaporization in the hygiene articles. A very significant advantage in connection with the inventive superabsorbents is the property of the UV-crosslinkable hotmelt adhesives of not tending to yellow during processing and crosslinking. This is especially advantageous when ultrathin or partly transparent hygiene articles are to be produced. The combination of the inventive superabsorbents with UV-crosslinkable hotmelt adhesives is therefore particularly advantageous. Suitable UV-crosslinkable hotmelt adhesives are, for example, described in EP 0 377 199 A2, EP 0 445 641 A1, U.S. Pat. No. 5,026,806, EP 0 655 465 A1 and EP 0 377 191 A2.

The inventive superabsorbent can also be used in other fields of industry in which liquids, especially water or aqueous solutions, are absorbed. These fields are, for example, storage, packaging, transport (as constituents of packaging material for water- or moisture-sensitive articles, for instance for flower transport, and also as protection against mechanical effects); animal hygiene (in cat litter); food packaging (transport of fish, fresh meat; absorption of water, blood in fresh fish or meat packaging); medicine (wound plasters, water-absorbing material for burn dressings or for other weeping wounds), cosmetics (carrier material for pharmaceutical chemicals and medicaments, rheumatic plasters, ultrasonic gel, cooling gel, cosmetic thickeners, sunscreen); thickeners for oil/water or water/oil emulsions; textiles (moisture regulation in textiles, shoe insoles, for evaporative cooling, for instance in protective clothing, gloves, headbands); chemical engineering applications (as a catalyst for organic reactions, for immobilization of large functional molecules such as enzymes, as an adhesive in agglomerations, heat stores, filtration aids, hydrophilic components in polymer laminates, dispersants, liquefiers); as assistants in powder injection molding, in the building and construction industry (installation, in loam-based renders, as a vibration-inhibiting medium, assistants in tunnel excavations in water-rich ground, cable sheathing); water treatment, waste removal, water removal (deicers, reusable sand bags); cleaning; agrochemical industry (irrigation, retention of melt water and dew deposits, composting additive, protection of forests from fungal/insect infestation, retarded release of active ingredients to plants); for firefighting or for fire protection; coextrusion agents in thermoplastic polymers (for example for hydrophilization of multilayer films); production of films and thermoplastic moldings which can absorb water (e.g. films which store rain and dew for agriculture; films comprising superabsorbents for maintaining freshness of fruit and vegetables which are packaged in moist films; superabsorbent-polystyrene coextrudates, for example for packaging foods such as meat, fish, poultry, fruit and vegetables); or as a carrier substance in active ingredient formulations (pharmaceuticals, crop protection).

The inventive articles for absorption of fluid differ from known examples in that they comprise the inventive superabsorbent.

Also found has been a process for producing articles for absorption of fluid, especially hygiene articles, which comprises using at least one inventive superabsorbent in the production of the article in question. In addition, processes for producing such articles using superabsorbents are known.

Test Methods

The superabsorbent is tested by the test methods described below.

The standard test methods referred to as "WSP" described below are described in: "Standard Test Methods for the Nonwovens Industry", 2005 edition, published jointly by the Worldwide Strategic Partners EDANA (European Disposables and Nonwovens Association, Avenue Eugene Plasky, 157, 1030 Brussels, Belgium, www.edana.org) and INDA (Association of the Nonwoven Fabrics Industry, 1100 Crescent Green, Suite 115, Cary, N.C. 27518, U.S.A., www.inda.org). This publication is obtainable both from EDANA and from INDA.

All measurements described below should, unless stated otherwise, be carried out at an ambient temperature of 23±2°

C. and a relative air humidity of 50±10%. The superabsorbent particles are mixed thoroughly before the measurement unless stated otherwise.

Centrifuge Retention Capacity (CRC)

The centrifuge retention capacity of the superabsorbent is determined by the standard test method No. WSP 241.5-05 "Centrifuge retention capacity".

Absorbency under a load of 0.3 psi (AUL0.3 psi)

The absorbency under a load of 2068 Pa (0.3 psi) of the superabsorbent is determined by the standard test method No. WSP 242.2-05 "Absorption under pressure".

Absorbency under a load of 0.7 psi (AUL0.7 psi)

The absorbency under a load of 4826 Pa (0.7 psi) of the superabsorbent is determined analogously to the standard test method No. WSP 242.2-05 "Absorption under pressure", except using a weight of 49 g/cm$^2$ (leads to a load of 0.7 psi) instead of a weight of 21 g/cm$^2$ (leads to a load of 0.3 psi).

Saline Flow Conductivity (SFC)

The saline flow conductivity of a swollen gel layer formed by the superabsorbent as a result of liquid absorption is determined under a pressure of 0.3 psi (2068 Pa), as described in EP 0 640 330 A1, as the gel layer permeability of a swollen gel layer of superabsorbent particles, the apparatus described in the aforementioned patent application on page 19 and in FIG. 8 being modified to the effect that the glass frit (40) is not used, the plunger (39) consists of the same polymer material as the cylinder (37) and now comprises 21 bores of equal size distributed homogeneously over the entire contact area. The procedure and evaluation of the measurement remain unchanged from EP 0 640 330 A1. The flow is detected automatically.

The saline flow conductivity (SFC) is calculated as follows:

$$SFC[\text{cm}^3\text{s/g}] = (Fg(t=0) \times L0)/(d \times A \times WP),$$

where Fg(t=0) is the flow of NaCl solution in g/s, which is obtained with reference to a linear regression analysis of the Fg(t) data of the flow determinations by extrapolation to t=0, L0 is the thickness of the gel layer in cm, d is the density of the NaCl solution in g/cm$^3$, A is the area of the gel layer in cm$^2$ and WP is the hydrostatic pressure over the gel layer in dyn/cm$^2$.

Free Swell Gel Bed Permeability (FSGBP)

The permeability is determined as described in US 2005/0 256 757 A1, paragraphs [0061] to [0075].

Moisture Content of the Hydrogel (Residual Moisture, Water Content)

The water content of the water-absorbing polymer particles is determined by the standard test method No. WSP 230.2-05 "Moisture content".

Mean Particle Size

The mean particle size of the product fraction is determined by the standard test method No. WSP 220.2-05 "Particle size distribution".

CIE Color Number (L a b)

The color analysis is carried out according to the CIELAB method (Hunterlab, Volume 8, 1996, Book 7, pages 1 to 4) with a "LabScan XE S/N LX17309" colorimeter (HunterLab, Reston, U.S.A.). This method describes the colors via the coordinates L, a and b of a three-dimensional system. L indicates the brightness, where L=0 means black and L=100 white. The values of a and b indicate the positions of the color on the red/green and yellow/blue color axes respectively, where +a represents red, −a represents green, +b represents yellow and −b represents blue. The HC60 value is calculated by the formula HC60=L−3b.

The color measurement corresponds to the three-area method according to DIN 5033-6.

Aging Test

Measurement 1 (initial color): A plastic dish of internal diameter 9 cm is overfilled with superabsorbent particles which are then smoothed flat with a blade over the edge, and the CIE color numbers and the HC60 value are determined.

Measurement 2 (after aging): A plastic dish of internal diameter 9 cm is filled with superabsorbent particles which are then smoothed flat with a blade over the edge. The dish is then placed open into a climate-controlled cabinet heated to 60° C. with constant relative air humidity of 86%. After 21 days have passed, the dish is taken out. After cooling to room temperature, the CIE color numbers are determined.

EXAMPLES

General Method I

Superabsorbents Produced by Static Polymerization

Examples 1-6 and Comparative Examples C1-C3

A 2 l stainless steel vessel was initially charged with 326.7 g of 50% by weight sodium hydroxide solution and 675 g of frozen deionized water. 392.0 g of acrylic acid were added while stirring, in the course of which the rate of addition was adjusted such that the temperature did not exceed 35° C. The mixture was then cooled with the aid of a cooling bath while stirring. When the temperature of the mixture had fallen to 20° C., 1.08 g of triacrylate of triethoxylated glycerol (Laromer® PO 9044V, BASF SE; Ludwigshafen, Germany), 0.041 g of 2-hydroxy-2-methyl-1-phenylpropan-1-one (DAROCUR® 1173, Ciba Specialty Chemicals Inc., Basle, Switzerland) and 0.014 g of 2,2-dimethoxy-1,2-diphenylethan-1-one (IRGACURE® 651, Ciba Specialty Chemicals Inc., Basle, Switzerland) were added. The mixture was cooled further and, on attainment of 15° C., the mixture was freed of oxygen by passing nitrogen through by means of a glass frit. On attainment of 0° C., 0.51 g of sodium persulfate (dissolved in 5 ml of water) and 0.06 g of hydrogen peroxide (dissolved in 6 ml of water) were added, and the monomer solution was transferred into a glass dish. The dimensions of the glass dish were such that a layer thickness of the monomer solution of 5 cm was established. Subsequently, 0.047 g of mixture of the sodium salt of 2-hydroxy-2-sulfinatoacetic acid, the disodium salt of 2-hydroxy-2-sulfonatoacetic acid and sodium bisulfite (Brüggolit® FF6, L. Brüggemann KG, Salzstrasse 131, 74076 Heilbronn, Germany), dissolved in 5 ml of water, was added and the monomer solution was stirred briefly with the aid of a glass rod. The glass dish containing the monomer solution was placed under a UV lamp (UV intensity=25 mW/cm$^2$), in the course of which polymerization set in. After 16 minutes, the gel obtained was ground three times with the aid of a commercial meat grinder with a 6 mm perforated disk, and dried in a laboratory drying cabinet at 160° C. for one hour. The product was then ground and the sieve fraction of 150-850 μm was obtained.

General Method II

Superabsorbents Polymerized in a Kneader

Examples 7-9 and Comparative Example C7

A Pflugschar® paddle dryer of capacity 5 l with a heating/cooling jacket (manufacturer: Gebr. Lödige Maschinenbau GmbH, Elsener-Strasse 7-9, 33102 Paderborn, Germany; model VT 5R-MK) was initially charged with 459 g of water, 213.9 g of acrylic acid, 1924.9 g of a 37.3% by weight sodium acrylate solution (100 mol % neutralized acrylic acid, i.e. without free acrylic acid or free sodium salt) and 2.52 g of triacrylate of triethoxylated glycerol (Laromer® PO 9044V, BASF SE; Ludwigshafen, Germany), and inertized by sparging with nitrogen for 20 minutes. The shaft of the reactor was constantly rotated at 96 revolutions per minute. At the same time, the reaction mixture was cooled externally such that the subsequent initiator addition was effected at approx. 20° C. Finally, 2.139 g of sodium persulfate (dissolved in 12.12 g of water), 0.046 g of ascorbic acid (dissolved in 9.12 g of water) and 0.127 g of 30% by weight aqueous hydrogen peroxide solution (diluted with 1.15 g of water) were also added in rapid succession to the kneader while stirring. The reaction set in rapidly and, on attainment of an internal temperature of 30° C., the jacket was heated with heat carrier medium at 80° C. in order to conduct the reaction to completion in a very substantially adiabatic manner. On attainment of the maximum temperature, the reactor was cooled again (cooling fluid at −12° C.), such that the gel formed cooled down to below 50° C., and it was then discharged. The gel was then dried in a laboratory drying cabinet at 160° C. for one hour. The product was then ground and the sieve fraction of 150-700 µm was obtained.

General Method III

Superabsorbents Produced by Dropletization Polymerization

Examples 10 and C10

14.3 kg of aqueous sodium acrylate solution (37.5% by weight solution in deionized water), 1.4 kg of acrylic acid and 350 g of deionized water were mixed with 18.5 g of Laromer® PO 9044V (glycerol-3E0 triacrylate). This solution was dropletized in a heated dropletization tower filled with a nitrogen atmosphere (180° C., height 12 m, diameter 2 m, gas velocity 0.1 m/s in cocurrent, dropletizer of diameter 40 mm, internal height 2 mm, and with a dropletizer plate with 60 bores each of diameter 200 µm) at a rate of 32 kg/h, in the course of which its temperature was 25° C. As the initiator, a 3% by weight solution of 2,2'-azobis[2-(2-imidazolin-2-yl) propane]dihydrochloride in deionized water at a temperature of 25° C. was metered into the monomer mixture at a metering rate of 2.2 kg/h by means of a static mixer connected directly to the dropletizer. The resulting polymer particles were sieved in order to remove any agglomerates formed. The sieve fraction from 150 to 850 µm was obtained as the product.

General Method IV

Dry Mixtures

Examples C13, 13, 15, C16, 16, 17, 19

The components to be mixed were introduced in a polyethylene sample bottle (capacity 500 ml) and mixed intimately with a tumbling mixer (model T2C; Willy A. Bachofen AG Maschinenfabrik, Basle; Switzerland) for 15 minutes.

Example C1 (Comparative)

According the above general method I, a superabsorbent was produced.

Example C2 (Comparative)

According to the above general method I, a superabsorbent was produced, except that 7.84 g of $Mg(OH)_2$ were additionally added to the monomer solution.

Example C3 (Comparative)

According to the above general method I, a superabsorbent was produced, except that only 72.8 g of the 50% by weight sodium hydroxide solution were used, and 117.6 g of $Ca(OH)_2$ and 802 g of ice instead of only 675 g of ice were additionally added to the monomer solution.

Example 1

According to the above general method I, a superabsorbent was produced, except that 3.92 g of $Ca(OH)_2$ were additionally added to the monomer solution.

Example 2

According to the above general method I, a superabsorbent was produced, except that 7.84 g of $Ca(OH)_2$ were additionally added to the monomer solution.

Example 3

According to the above general method I, a superabsorbent was produced, except that only 284.4 g of the 50% by weight sodium hydroxide solution were used, and 19.6 g of $Ca(OH)_2$ were additionally added to the monomer solution.

Example 4

According to the above general method I, a superabsorbent was produced, except that 7.84 g $Sr(OH)_2$ were additionally added to the monomer solution.

Example 5

According to the above general method I, a superabsorbent was produced, except that 7.84 g of $Ba(OH)_2$ were additionally added to the monomer solution.

Example 6

According to the above general method I, a superabsorbent was produced, except that 7.84 g of $Ca(OH)_2$, dispersed in 75 ml of water, were added to the gel comminuted for the first time in the meat grinder. This mixture was homogenized by manual kneading and then ground twice more in the meat grinder.

The superabsorbents thus produced were subjected to the aging test; in addition, CRC and AUL 0.7 psi were measured. The results are compiled in Table 1.

The examples show that inventive superabsorbents exhibit good absorption performance and are significantly lighter-colored and less discolored both before and after aging. Example C3 shows that increasing the calcium content further achieves outstanding color values, especially after aging, and such a superabsorbent also has high gel stability, but has an undesirably low absorption capacity.

TABLE 1

| Example | Additive*) | CRC [g/g] | AUL 0.7 psi [g/g] | Initial color | | | | After aging | | | |
|---|---|---|---|---|---|---|---|---|---|---|---|
| | | | | L | a | b | HC 60 | L | a | b | HC 60 |
| C1 | — | 39.4 | 8.5 | 87.4 | 0.1 | 8.4 | 62.2 | 68.5 | 2.2 | 13.0 | 29.4 |
| C2 | 2% by wt. of Mg(OH)$_2$ | 37.4 | 8.3 | 87.6 | 0.1 | 8.2 | 63.0 | 70.2 | 1.9 | 12.8 | 31.8 |
| C3 | 30% by wt. of Ca(OH)$_2$ | 22.8 | 12.4 | 92.1 | −0.4 | 5.9 | 74.4 | 83.6 | 0.4 | 9.8 | 54.2 |
| 1 | 1% by wt. of Ca(OH)$_2$ | 37.8 | 8.6 | 87.9 | 0.1 | 7.8 | 64.5 | 75.6 | 1.5 | 11.6 | 40.0 |
| 2 | 2% by wt. of Ca(OH)$_2$ | 37.2 | 8.8 | 89.6 | −0.1 | 6.6 | 69.9 | 79.0 | 0.8 | 11.1 | 45.8 |
| 3 | 5% by wt. of Ca(OH)$_2$ | 35.8 | 9.5 | 90.2 | −0.2 | 6.3 | 71.3 | 81.2 | 0.6 | 10.8 | 48.8 |
| 4 | 2% by wt. of Sr(OH)$_2$ | 37.5 | 8.4 | 89.7 | −0.1 | 7.2 | 68.1 | 80.1 | 0.7 | 11.0 | 47.1 |
| 5 | 2% by wt. of Ba(OH)$_2$ | 37.6 | 8.7 | 89.8 | −0.2 | 6.7 | 69.7 | 80.2 | 0.6 | 10.9 | 47.5 |
| 6 | 2% by wt. of Ca(OH)$_2$ | 37.4 | 8.6 | 87.8 | 0.1 | 8.2 | 63.2 | 72.7 | 1.6 | 12.2 | 36.1 |

*)amount based in each case on acrylic acid used

Example C7 (Comparative)

According to the above general method II, a superabsorbent was produced.

Example 7

According to the above general method II, a superabsorbent was produced, except that 16.0 g of CaCO$_3$ were additionally added to the monomer solution, and only 478 g of ice instead of 459 g, and 244.3 g of acrylic acid instead of 213.9 g, were used.

Example 8

According to the above general method II, a superabsorbent was produced, except that 320.0 g of a 5% by weight aqueous calcium lactate solution were added to the monomer solution, and only 155 g of ice instead of 459 g, were used.

Example 9

According to the above general method II, a superabsorbent was produced, except that, on attainment of the maximum temperature, 22.5 g of CaSO$_4$.2H$_2$O, dispersed in 100 ml of water, were first added to the gel in the kneader and then kneading was continued for 10 minutes further before the cooling was commenced.

The superabsorbents thus produced were subjected to the aging test; in addition, CRC and AUL 0.7 psi of the unaged superabsorbent were measured. The results are compiled in Table 2. The examples show that inventive superabsorbents exhibit good absorption performance and are significantly lighter-colored and less discolored both before and after aging.

Example C10 (Comparative)

According to the above general method III, a superabsorbent was produced.

Example 10

According to the above general method III, a superabsorbent was produced, except that 138 g of Ca(OH)$_2$ were additionally added to the monomer solution, and 570 g of water instead of 350 g, and 1.77 kg of acrylic acid instead of 1.4 kg, were used.

The superabsorbents thus produced were subjected to the aging test; in addition, CRC and AUL 0.7 psi of the unaged superabsorbent were measured. The results are compiled in Table 3. The examples show that inventive superabsorbents exhibit good absorption performance and are significantly lighter-colored and less discolored both before and after aging.

TABLE 2

| Example | Additive*) | CRC [g/g] | AUL 0.7 psi [g/g] | Initial color | | | | After aging | | | |
|---|---|---|---|---|---|---|---|---|---|---|---|
| | | | | L | a | b | HC 60 | L | a | b | HC 60 |
| C7 | — | 39.4 | 8.5 | 87.4 | 0.1 | 8.4 | 62.2 | 68.5 | 2.2 | 13.0 | 29.4 |
| 7 | 2% by wt. of CaCO$_3$ | 35.6 | 9.4 | 92.9 | −0.8 | 6.2 | 74.3 | 82.3 | 0.6 | 10.5 | 50.8 |
| 8 | 2.1% by wt. of Ca(O$_2$CCH(OH)CH$_3$)$_2$ | 35.4 | 9.1 | 93.1 | −0.9 | 6.1 | 74.8 | 82.2 | 0.7 | 10.6 | 50.4 |
| 9 | 2.3% by wt. of CaSO$_4$**) | 35.8 | 9.0 | 92.8 | −0.8 | 6.3 | 73.9 | 77.5 | 1.9 | 11.8 | 42.1 |

*)amount based in each case on acrylic acid used, sodium acrylate counted as acrylic acid.
**)calculated without water of crystallization

TABLE 3

| Example | Additive*) | CRC [g/g] | AUL 0.7 psi [g/g] | Initial color | | | | After aging | | | |
|---|---|---|---|---|---|---|---|---|---|---|---|
| | | | | L | a | b | HC 60 | L | a | b | HC 60 |
| C10 | — | 30.5 | 22.8 | 93.4 | 0.8 | 2.3 | 86.4 | 71.0 | 3.4 | 17.2 | 19.4 |
| 10 | 2.5% by wt. of Ca(OH)$_2$ | 28.9 | 23.3 | 93.4 | 0.6 | 2.1 | 87.1 | 80.7 | 1.2 | 12.1 | 44.4 |

*)amount based in each case on acrylic acid used, sodium acrylate counted as acrylic acid.

Example C11 (Comparative)

For surface postcrosslinking, the superabsorbent from example C1 was coated in a Pflugschar® plowshare mixer with a heating jacket (manufacturer: Gebr. Lödige Maschinenbau GmbH, Elsener-Strasse 7-9, 33102 Paderborn, Germany; Type M5), at room temperature and a shaft speed of 450 revolutions per minute, by means of a two-substance spraying nozzle, with a mixture of 0.10% by weight of ethylene glycol diglycidyl ether (Denacol® EX-810 from Nagase ChemteX Corporation, Osaka, Japan), 1.50% by weight of 1,2-propanediol, 2.8% by weight of water and 0.4% by weight of aqueous aluminum sulfate solution (26.8% by weight), based in each case on the base polymer.

After the spray application, the product temperature was increased to 150° C. and the reaction mixture was kept at this temperature and a shaft speed of 80 revolutions per minute for 60 minutes. The resulting product was again allowed to cool to room temperature and screened. The surface postcrosslinked superabsorbent was obtained as the screening fraction with particle sizes between 150 µm and 850 µm.

Example 11

Example C11 was repeated with the superabsorbent from example 2.

Example CV12 (Comparative)

A laboratory mixer (manufacturer: Waring Products, Inc., Torrington, Conn., U.S.A., model 34 BL 99 (8012)) with two opposite rounded mixing blades and baffles on the lid (comparable results are also achieved in many other mixers with good mixing during the introduction of the postcrosslinking solution, though it should be ensured that the stirrer units do not comminute the superabsorbent—the stirrer speed should be set accordingly) was initially charged with 20 g of the superabsorbent from example C7. A disposable syringe was used to spray a mixture of 0.025 g of N-(2-hydroxyethyl)-2-oxazolidinone, 0.30 g of water, 0.30 g of 1,3-propanediol, 0.0006 g of sorbitan monococoate ("Span® 20") and 1.12 g of a 12.5% by weight aqueous aluminum lactate solution onto the mixed superabsorbent at a moderate stirrer speed of the mixer.

The moist superabsorbent particles were homogenized once again with a spatula, then distributed homogeneously in a Petri dish with an internal diameter of 18.5 cm, and heat-treated at 175° C. in a laboratory drying cabinet for 90 minutes. The post-crosslinked polymer particles were freed of lumps by means of a 700 µm sieve.

Example 12

Example C12 was repeated with the superabsorbent from example 7.

Example C13 (Comparative)

100 g of the superabsorbent from example C10 were mixed with 0.5 g of a precipitated silica (Sipernat® 22 S, Evonik Degussa GmbH; Frankfurt am Main; Germany) according to general method IV.

Example 13

Example C13 was repeated with the superabsorbent from example 10.

Example C14 (Comparative)

The superabsorbent from example C11 was coated in a Pflugschar® plowshare mixer (manufacturer: Gebr. Lödige Maschinenbau GmbH, Elsener-Strasse 7-9, 33102 Paderborn, Germany; model M5) with 2.0% by weight (based on the superabsorbent) of a 7.5% by weight solution of sodium hypophosphite by means of a two-substance spray nozzle at room temperature and a shaft speed of 250 revolutions per minute. After the spray application, mixing was continued at a shaft speed of 80 revolutions per minute for another 15 minutes and the mixture was freed of lumps by means of an 850 µm sieve.

Example 14

Example C14 was repeated with the superabsorbent from example 11.

Example 15

100 g of the superabsorbent from example 11 were mixed with 0.025 g of 2,6-di-tert-butyl-4-methylphenol according to general method IV.

Example C16 (Comparative)

100 g of the superabsorbent from example C12 were mixed with 0.025 g of calcium bis[monoethyl(3,5-di-tert-butyl-4-hydroxybenzyl)phosphonate] according to general method IV.

Example 16

Example C16 was repeated with the superabsorbent from example 12.

Example 17

100 g of the superabsorbent from example 12 were mixed with 0.025 g of tris(2,4-di-tert-butylphenyl)phosphite according to general method IV.

Example C18 (Comparative)

The superabsorbent from example C10 was coated in a Pflugschar® plowshare mixer (manufacturer: Gebr. Lödige Maschinenbau GmbH, Elsener-Strasse 7-9, 33102 Paderborn, Germany; model M5) at room temperature and a shaft speed of 250 revolutions per minute with 2.0% by weight (based on the superabsorbent) of a 1.75% by weight aqueous solution of Brüggolit® FF7 by means of a two-substance nozzle. After the spray application, mixing was continued for another 15 minutes at a shaft speed of 80 revolutions per minute and the mixture was freed of lumps by means of an 850 µm sieve.

Example 18

Example $C_{18}$ was repeated with the superabsorbent from example 10.

Example 19

100 g of the superabsorbent from example 10 were mixed with 0.025 g of 3,9-bis(octa-decyloxy)-2,4,8,10-tetraoxa-3,9-diphosphaspiro[5.5]undecane according to general method IV.

The superabsorbents thus produced were subjected to the aging test; in addition, CRC, AUL 0.7 psi, SFC and FSGBP of some of the unaged superabsorbents were measured. The results are compiled in Table 4. The examples show that the calcium-comprising superabsorbents exhibit good absorption performance and are significantly lighter-colored and less discolored especially after aging.

TABLE 4

| Example | Comment | CRC [g/g] | AUL 0.7 psi [g/g] | SFC [$10^{-7}cm^3s/g$] | FSGBP [Da] | After aging L | a | b | HC 60 |
|---|---|---|---|---|---|---|---|---|---|
| C11 | Ex. C1 + Denacol | 31.6 | 22.9 | 25 | 15 | 68.1 | 3.0 | 13.2 | 28.5 |
| 11 | Ex. 2 + Denacol | 30.4 | 23.1 | 28 | 13 | 78.8 | 1.0 | 11.4 | 44.6 |
| C12 | Ex. C7 + oxazolidone | 28.7 | 24.2 | 112 | 12 | 71.2 | 4.9 | 13.9 | 29.5 |
| 12 | Ex. 7 + oxazolidone | 28.2 | 24.1 | 122 | 14 | 80.9 | 1.1 | 11.3 | 47.0 |
| C13 | Ex. C10 + Sipernat | 30.6 | 19.4 | 42 | 22 | 71.3 | 3.2 | 16.9 | 20.6 |
| 13 | Ex. 10 + Sipernat | 29.2 | 19.7 | 46 | 25 | 81.0 | 1.3 | 11.9 | 45.3 |
| C14 | Ex. C11 + hypophosphite | | | | | 74.2 | 1.5 | 12.3 | 37.3 |
| 14 | Ex. 11 + hypophosphite | | | | | 83.6 | 0.4 | 10.6 | 51.8 |
| 15 | Ex. 11 + phenol | | | | | 85.1 | 0.5 | 10.2 | 54.5 |
| C16 | Ex. C12 + phosphonate | | | | | 79.8 | 0.8 | 11.7 | 44.7 |
| 16 | Ex. 12 + phosphonate | | | | | 86.2 | 0.3 | 10.0 | 56.2 |
| 17 | Ex. 12 + phosphite | | | | | 84.5 | 0.6 | 10.8 | 52.1 |
| C18 | Ex. C10 + FF7 | | | | | 76.3 | 2.2 | 13.4 | 36.1 |
| 18 | Ex. 10 + FF7 | | | | | 83.1 | 0.8 | 11.2 | 49.5 |
| 19 | Ex. 10 − FF7 | | | | | 84.9 | 0.6 | 10.4 | 53.7 |

The invention claimed is:

1. A superabsorbent produced by polymerizing a monomer mixture comprising (a) at least one ethylenically unsaturated monomer bearing at least one acid group neutralized from 25 to 95 mol % as an alkali metal or ammonium salt and (b) at least 1% by weight and at most 5%, by weight, of at least one alkaline earth metal salt (calculated without water of crystallization) based on the total amount of ethylenically unsaturated monomer bearing at least one acid group (calculated as the free acid), the at least one alkaline earth metal salt selected from the salts of calcium, strontium, and barium, and the at least one alkaline earth metal salt having been added after neutralization of the monomer and during the polymerization and/or, if the polymerization is followed by a separate drying step, to the polymer before the drying.

2. The superabsorbent according to claim 1, wherein the alkaline earth metal salt is a hydroxide, carbonate, lactate, or sulfate.

3. The superabsorbent according to claim 1, wherein the monomer is acrylic acid.

4. The superabsorbent according to claim 1, to which has additionally been added at least one compound selected from derivatives of sulfinic acid, sterically hindered phenols, organic phosphites and phosphonates, and/or at least one inorganic water-insoluble particulate solid.

5. The superabsorbent according to claim 1, which is surface post-crosslinked.

6. The superabsorbent according to claim 1, wherein the at least one ethylenically unsaturated monomer bearing at least one acid group is neutralized 50 to 80 mol % as an alkali metal or ammonium salt.

7. The superabsorbent according to claim 1, wherein the at least one ethylenically unsaturated monomer bearing at least one acid group is neutralized 65 to 72 mol % as an alkali metal or ammonium salt.

8. The superabsorbent according to claim 1, wherein the at least one ethylenically unsaturated monomer bearing at least one acid group is neutralized 50 to 80 mol % as an alkali metal or ammonium salt.

9. The superabsorbent according to claim 1, wherein the at least one ethylenically unsaturated monomer bearing at least one acid group is neutralized 65 to 72 mol % as an alkali metal or ammonium salt.

10. A process for producing a superabsorbent defined in claim 1 by polymerizing a monomer mixture comprising at least one ethylenically unsaturated monomer bearing at least one acid group neutralized from 25 to 95 mol % as an alkali metal or ammonium salt, which comprises adding at least 1% by weight and at most 5% by weight, of at least one alkaline earth metal salt (calculated without water of crystallization) based on the total amount of ethylenically unsaturated monomers bearing at least one acid group to the neutralized monomer mixture during the polymerization and/or, if the polymerization is followed by a separate drying step, to the polymerization before the drying,
the at least one alkaline earth metal salt selected from the salts of calcium, strontium, and barium.

11. The superabsorbent according to claim 10, wherein the alkaline earth metal salt is added to the neutralized monomer mixture which is polymerized to give the superabsorbent.

12. An article for absorbing fluids, comprising a superabsorbent defined in claim 1.

13. A superabsorbent produced by polymerizing a monomer mixture comprising (a) at least one ethylenically unsaturated monomer bearing at least one acid group neutralized from 25 to 95 mol % as an alkali metal or ammonium salt and (b) at least 1% by weight and at most 5%, by weight, of at least one alkaline earth metal salt (calculated without water of crystallization) based on the total amount of ethylenically unsaturated monomer bearing at least one acid group (calculated as the free acid), the at least one alkaline earth metal salt selected from the salts of calcium, strontium, and barium, and the at least one alkaline earth metal salt having been added to the neutralized monomer before-the polymerization.

14. The process according to claim 13, wherein at least one compound selected from derivatives of sulfinic acid, sterically hindered phenols, organic phosphites and phosphonates, and/or at least one inorganic water-insoluble particulate solid is added during or after the preparation of the superabsorbent.

15. The superabsorbent according to claim 13, wherein the alkaline earth metal salt is a hydroxide, carbonate, lactate, or sulfate.

16. The superabsorbent according to claim 13, wherein the monomer is acrylic acid.

17. The superabsorbent according to claim 13, which is surface post-crosslinked.

18. A process for producing a superabsorbent defined in claim 13 by polymerizing a monomer mixture comprising at least one ethylenically unsaturated monomer bearing at least one acid group neutralized from 25 to 95 mol % as an alkali metal salt or ammonium, which comprises adding at least 1% by weight and at most 5% by weight, of at least one alkaline earth metal salt (calculated without water of crystallization) based on the total amount of ethylenically unsaturated monomers bearing at least one acid group to the neutralized monomer mixture before the polymerization, the at least one alkaline earth metal salt selected from the salts of calcium, strontium, and barium.

19. The process according to claim 18, wherein at least one compound selected from derivatives of sulfinic acid, sterically hindered phenols, organic phosphites and phosphonates, and/or at least one inorganic water-insoluble particulate solid is added during or after the preparation of the superabsorbent.

* * * * *